(12) United States Patent
Ackerman et al.

(10) Patent No.: US 12,365,951 B2
(45) Date of Patent: Jul. 22, 2025

(54) DIAGNOSTIC TESTING USING MICROBIAL BIOMARKERS TO CLASSIFY PELVIC AND BLADDER PAIN

(71) Applicant: CEDARS-SINAI MEDICAL CENTER, Los Angeles, CA (US)

(72) Inventors: Anne Lenore Ackerman, Los Angeles, CA (US); David M. Underhill, Tarzana, CA (US)

(73) Assignee: Cedars-Sinai Medical Center, Los Angeles, CA (US)

( * ) Notice: Subject to any disclaimer, the term of this patent is extended or adjusted under 35 U.S.C. 154(b) by 123 days.

(21) Appl. No.: 17/525,112

(22) Filed: Nov. 12, 2021

(65) Prior Publication Data

US 2022/0145372 A1     May 12, 2022

Related U.S. Application Data

(60) Provisional application No. 63/112,844, filed on Nov. 12, 2020.

(51) Int. Cl.
    *C12Q 1/689*          (2018.01)
(52) U.S. Cl.
    CPC .................................. *C12Q 1/689* (2013.01)
(58) Field of Classification Search
    None
    See application file for complete search history.

(56) References Cited

U.S. PATENT DOCUMENTS

2011/0014205 A1*   1/2011   Schaeffer ............. A61K 31/537
                                                                514/415
2017/0007560 A1*   1/2017   Himes ..................... A61P 13/00

OTHER PUBLICATIONS

Rudick, Uropathogenic *Escherichia coli* Induces Chronic Pelvic Pain, Infection and Immunity, 79(2): 628-635, 2011. (Year: 2011).*
Millipore Sigma, Coliforms, *E. coli* & Enterobacteriaceae, 2023. (Year: 2023).*
Mandar, Seminal Microbiome in men with and without prostatitis, International Journal of Urology, 24, 211-216, 2017. (Year: 2017).*
Ackerman, Microbial Composition Defined Pelvic Pain Phenotypes in Reproductive-Age Women, Journal of Urology, 2023, 4S, e100, May 15, 2020. (Year: 2020).*
Abernethy, Urinary Microbiome and Cytokine Levels in Women with Interstitial Cystitis, Obstetrics & Gynecology, 129(3): 500-506, 2017. (Year: 2017).*
Nickel, Assessment of the Lower Urinary Tract Microbiota during Symptom Flare in Women with Urologic Chronic Pelvic Pain Syndrome: A MAPP Network Study, Journal of Urology, 195, 356-362, 2016. (Year: 2016).*

* cited by examiner

*Primary Examiner* — Angela M. Bertagna
*Assistant Examiner* — Carolyn L Greene
(74) *Attorney, Agent, or Firm* — Linda B. Huber; Nixon Peabody LLP

(57) ABSTRACT

The invention describes methods for a method of detecting levels of one or more microorganisms, selecting treatment for interstitial cystitis, pelvic pain, bladder pain and myofascial pain and treating interstitial cystitis, pelvic pain, bladder pain and myofascial pain. The invention also describes detecting bacterial phenotype and kits.

21 Claims, 7 Drawing Sheets

Specification includes a Sequence Listing.

FIG. 3A
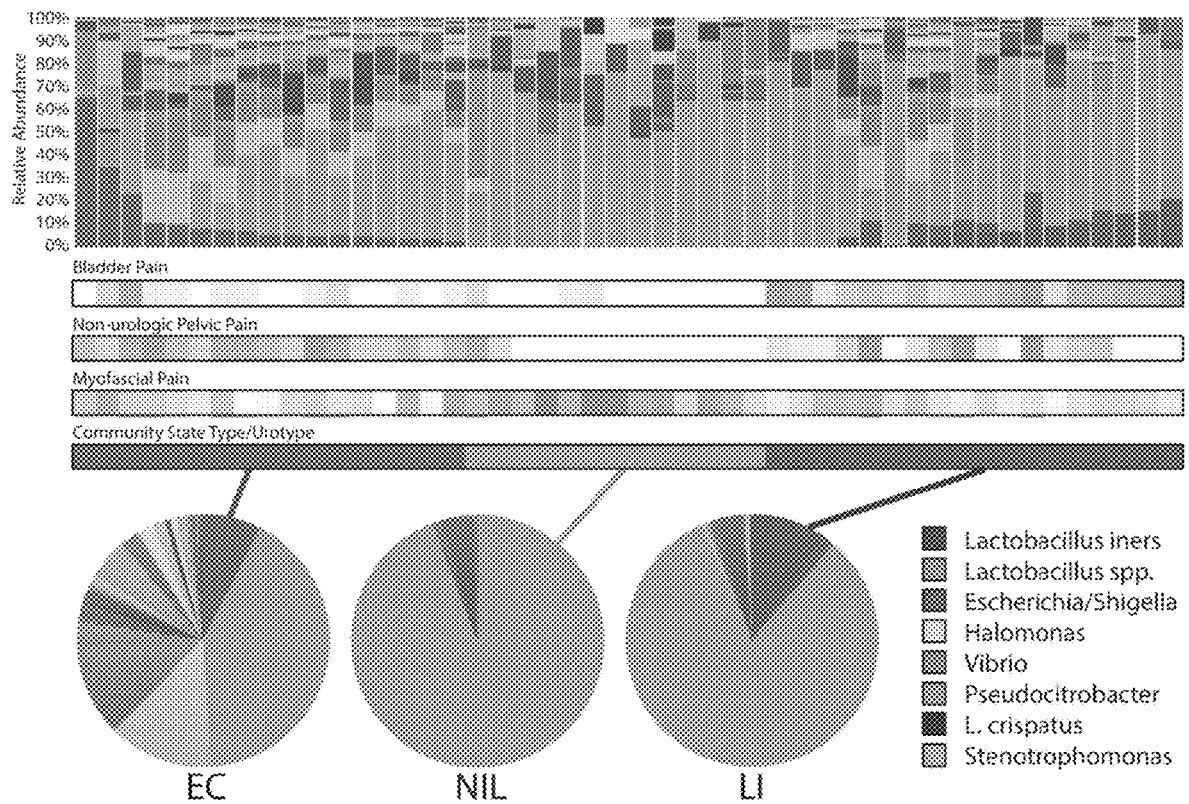
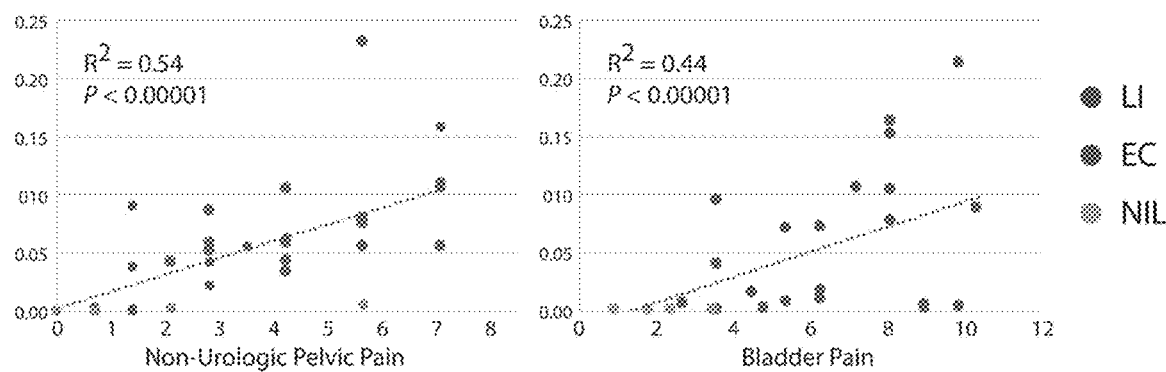
FIG. 3B

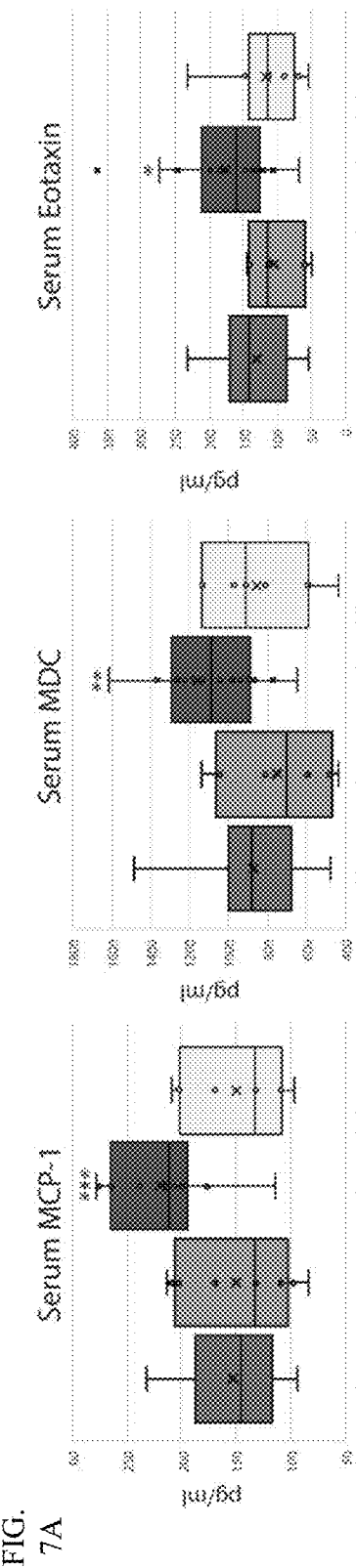
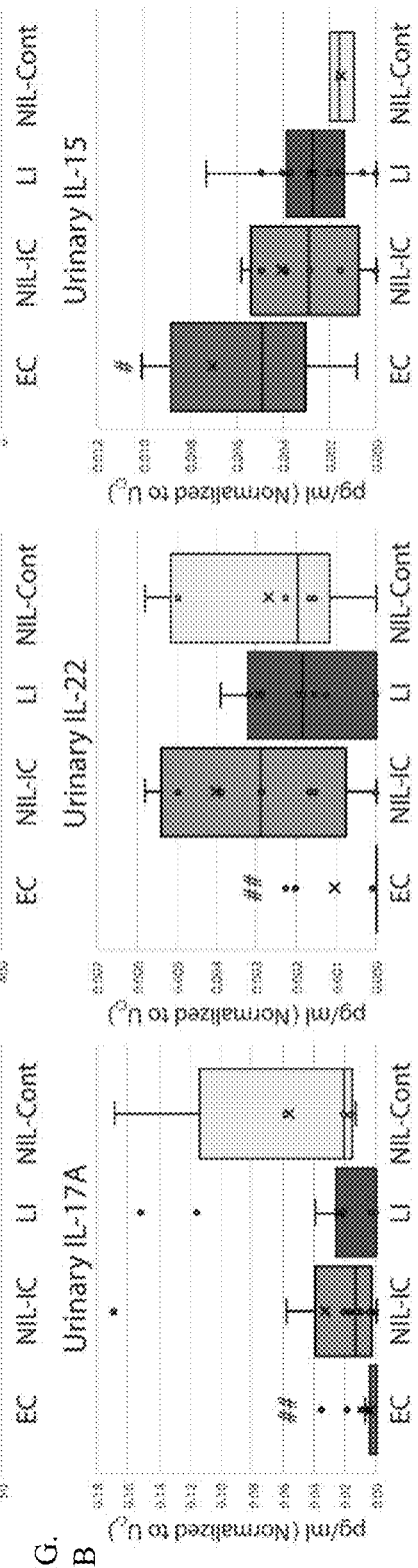
FIG. 7A
FIG. 7B

SEQUENCE LISTING

<160> NUMBER OF SEQ ID NOS: 8

<210> SEQ ID NO 1
<211> LENGTH: 20
<212> TYPE: DNA
<213> ORGANISM: Artificial Sequence
<220> FEATURE:
<223> OTHER INFORMATION: synthetic construct

<400> SEQUENCE: 1
agagtttgat cmtggctcag                                       20

<210> SEQ ID NO 2
<211> LENGTH: 15
<212> TYPE: DNA
<213> ORGANISM: Artificial Sequence
<220> FEATURE:
<223> OTHER INFORMATION: synthetic construct

<400> SEQUENCE: 2
ctgctgccty ccgta                                            15

<210> SEQ ID NO 3
<211> LENGTH: 21
<212> TYPE: DNA
<213> ORGANISM: Artificial Sequence
<220> FEATURE:
<223> OTHER INFORMATION: synthetic construct

<400> SEQUENCE: 3
actcctacgg gaggcagcag t                                     21

<210> SEQ ID NO 4
<211> LENGTH: 18
<212> TYPE: DNA
<213> ORGANISM: Artificial Sequence
<220> FEATURE:
<223> OTHER INFORMATION: synthetic construct

<400> SEQUENCE: 4
attaccgcgg ctgctggc                                         18

<210> SEQ ID NO 5
<211> LENGTH: 25
<212> TYPE: DNA
<213> ORGANISM: Artificial Sequence
<220> FEATURE:
<223> OTHER INFORMATION: synthetic construct

<400> SEQUENCE: 5
ggaagaagct tgcttctttg ctgac                                 25

<210> SEQ ID NO 6
<211> LENGTH: 26
<212> TYPE: DNA
<213> ORGANISM: Artificial Sequence
<220> FEATURE:
<223> OTHER INFORMATION: synthetic construct

<400> SEQUENCE: 6
agcccgggga tttcacatct gactta                                26

<210> SEQ ID NO 7
<211> LENGTH: 18
<212> TYPE: DNA
<213> ORGANISM: Artificial Sequence

```
<220> FEATURE:
<223> OTHER INFORMATION: synthetic construct

<400> SEQUENCE: 7
gtctgccttg aagatcgg                                                    18

<210> SEQ ID NO 8
<211> LENGTH: 19
<212> TYPE: DNA
<213> ORGANISM: Artificial Sequence
<220> FEATURE:
<223> OTHER INFORMATION: synthetic construct

<400> SEQUENCE: 8
acagttgata ggcatcatc                                                   19
```

DIAGNOSTIC TESTING USING MICROBIAL BIOMARKERS TO CLASSIFY PELVIC AND BLADDER PAIN

CROSS-REFERENCE TO RELATED APPLICATIONS

This application includes a claim of priority under 35 U.S.C. § 119(e) to U.S. provisional patent application No. 63/112,844, filed Nov. 12, 2020, the entirety of which is hereby incorporated by reference.

STATEMENT REGARDING FEDERALLY SPONSORED RESEARCH OR DEVELOPMENT

This invention was made with Government support under award number W81XWH-17-1-0433 awarded by the Department of Defense. The Government has certain rights in the invention.

REFERENCE TO A SEQUENCE LISTING

This application containing an ASCII text file, with a sequence listing, named "SequenceListing065472-000816US00_ST25", created on Nov. 10, 2021, and having 1,879 bytes in size is in incorporated herein by reference as though fully set forth in its entirety.

FIELD OF INVENTION

This invention relates to the detection and treatment of pelvic and bladder pain.

BACKGROUND

All publications herein are incorporated by reference to the same extent as if each individual publication or patent application was specifically and individually indicated to be incorporated by reference. The following description includes information that may be useful in understanding the present invention. It is not an admission that any of the information provided herein is prior art or relevant to the presently claimed invention, or that any publication specifically or implicitly referenced is prior art.

In reproductive-age women, there is significant symptomatic overlap between interstitial cystitis/bladder pain syndrome, chronic pelvic pain, overactive bladder syndrome (OAB), vulvodynia, and endometriosis leading to frequent misdiagnosis and delayed care. The epidemiology of pelvic pain suggests a microbial involvement in its etiology, but previous studies have failed to definitively identify specific bacteria associated with pain diagnoses.

Interstitial cystitis/bladder pain syndrome and other chronic pelvic pain syndromes are highly refractory to treatment. Many patients never receive a specific diagnosis, and even those who do eventually get a diagnosis are frequently misdiagnosed and will often experience profound delays in diagnosis of as much as 9 years. Even after diagnosis, clinicians must employ a process of trial and error to eventually be able to find an effective treatment. These substantial barriers to appropriate care are the cause of a lack of testing to identify these conditions and any prognostic testing or information to help providers identify which therapies may be most beneficial for patients.

As such, there is a need in the art to provide ways to distinguish each of these conditions and to determine treatments that would be appropriate.

SUMMARY OF THE INVENTION

The following embodiments and aspects thereof are described and illustrated in conjunction with compositions and methods which are meant to be exemplary and illustrative, not limiting in scope.

Various embodiments of the present invention provide for a method of detecting levels of one or more microorganisms in a subject in need thereof, comprising: assaying a biological sample obtained from the subject, wherein the subject has one or more symptoms of interstitial cystitis, pelvic pain or bladder pain; and detecting the levels of one or more microorganisms in the biological sample.

In various embodiments, the one or more microorganisms can comprise *Lactobacillus* and Enterobacteriaceae bacteria. In various embodiments, the one or more microorganisms can comprise *Lactobacillus iners* (*L. iners*), *E. coli*, or both.

In various embodiments, the one or more symptoms can be one or more symptoms of interstitial cystitis, pelvic pain or bladder pain or myofascial pain.

In various embodiments, the one or more organisms can comprise non-*iners Lactobacilli* (NIL), *Lactobacillus iners*, Enterobacteriaceae, or *Shigella*. In various embodiments, the one or more microorganisms can comprise non-*iners Lactobacilli* (NIL), *Lactobacillus iners* (*L. iners*), *E. coli*, or *Shigella*.

In various embodiments, the biological sample is urine.

In various embodiments, the method of the present invention can further comprise comparing each detected level of the one or more microorganisms to each microorganism's reference level.

In various embodiments, the subject may not have an active urinary tract infection as defined by a negative bacterial culture.

In various embodiments, the assay can comprise using a technique selected from the group consisting of qPCR, RT-PCR, and next-generation sequencing.

Various embodiments of the present invention provide for a method for treating interstitial cystitis, pelvic pain or bladder pain, comprising: administering a local bladder therapy to a subject who has been detected to have a level of *Lactobacillus iners* (*L. iners*) higher than a reference level.

In various embodiments, the methods of the present invention can further comprise: obtaining or requesting the results of an analysis of levels of one or more microorganisms in a biological sample obtained from the subject before administering the local bladder therapy.

In various embodiments, the biological sample can be urine.

In various embodiments, the local bladder therapy can be a bladder instillation. In various embodiments, the bladder instillation comprises instilling an agent selected from the group consisting of alkalinized lidocaine and heparin, dimethyl sulfoxide (DMSO), sodium hyaluronate, heparin, a bladder cocktail, and an experimental solution. In various embodiments, the bladder cocktail can comprise bupivacaine, heparin, hydrocortisone, lidocaine jelly, triamcinolone, gentamicin, lidocaine, sodium bicarbonate, gentamicin, DMSO, triamcinolone, or combinations thereof.

In various embodiments, the experimental solution can be selected from the group consisting of PSD597, URG101, URACYST (formulation of sterlie sodium chondroitin sulfate solution (2.0%)); LIPELLA liposomes, misoprostol, and combinations thereof.

In various embodiments, the subject may not have an active urinary tract infection as defined by a negative bacterial culture.

In various embodiments, *Lactobacillus iners* (*L. iners*) or *E. coli* can each be independently detected by using a technique selected from the group consisting of qPCR, RT-PCR, and next-generation sequencing.

Various embodiments of the present invention provide for a method for treating interstitial cystitis, pelvic pain, bladder pain, or myofascial pain, comprising: administering a musculoskeletal-directed therapy to a subject who has been detected to have both a level of *Lactobacillus iners* (*L. iners*) lower than a reference level, and a level of *E. coli* lower than a reference level.

Various embodiments of the present invention provide for a method of selecting a treatment for a subject having interstitial cystitis, pelvic pain, bladder pain, or myofascial pain comprising detecting levels of one or more microorganisms in a biological sample obtained from a subject in need thereof; and selecting local bladder treatment for subjects with levels of *Lactobacillus iners* (*L. iners*) that are higher than a reference level indicates a local bladder treatment for the subject, or selecting a non-local bladder treatment for subjects with levels of Enterobacteriaceae bacteria that are higher than a reference level indicates based on the understanding that the subject will be refractory to local bladder therapies, or selecting a musculoskeletal-directed therapy to a subject who has been detected to have both a level of *Lactobacillus iners* (*L. iners*) lower than a reference level, and a level of *E. coli* lower than a reference level.

Other features and advantages of the invention will become apparent from the following detailed description, taken in conjunction with the accompanying drawings, which illustrate, by way of example, various features of embodiments of the invention.

BRIEF DESCRIPTION OF THE FIGURES

Exemplary embodiments are illustrated in referenced figures. It is intended that the embodiments and figures disclosed herein are to be considered illustrative rather than restrictive.

FIG. 3A-3B shows correlation of microbial patterns with pain phenotypes. (3A) The individual urinary microbial compositions of an independent verification population of 49 additional subjects, all with bladder pain, are exhibited in stacked box plots, ordered by urotype. This independent population reiterated the correlation of LI with bladder pain, EC with non-urologic pelvic pain, and NIL with myofascial pain, for which the severity of each is quantitated in the heat bars below the plot. The pie charts below indicate the median microbial composition for each urotype designated in the color bar. The NIL group and LI groups differed minimally, except for the presence of *Lactobacillus iners*. The EC group was significantly more diverse, frequently featuring *Vibrio* and *Halomonas* spp. (3B) Scatter plots of NUPP and BPS symptom severity demonstrated significant correlations with bacterial relative abundance of *Escherichia* (left) and *L. iners* (right), respectively. Linear regression analysis demonstrated that these associations were statistically significant for both associations.

FIG. 7A-7B shows that proteomic analysis of urine and serum samples reveals distinct inflammatory patterns associated with IC/BPS subtypes. Box and whisker plots display the levels of the designated cytokine for each phenotype/urotype that was significantly different between groups. (7A) Serum chemokines were elevated in the LI group. (7B) Urinary cytokine levels were normalized to urinary creatinine before analysis, revealing decreased levels of IL-17A and IL-22 as well as elevated IL-15. \*\*\*: p=0.0001; \*\*: p=0.006; \*: p=0.02; ##: p=0.03; #: p=0.01.

DESCRIPTION OF THE INVENTION

Figure 1:
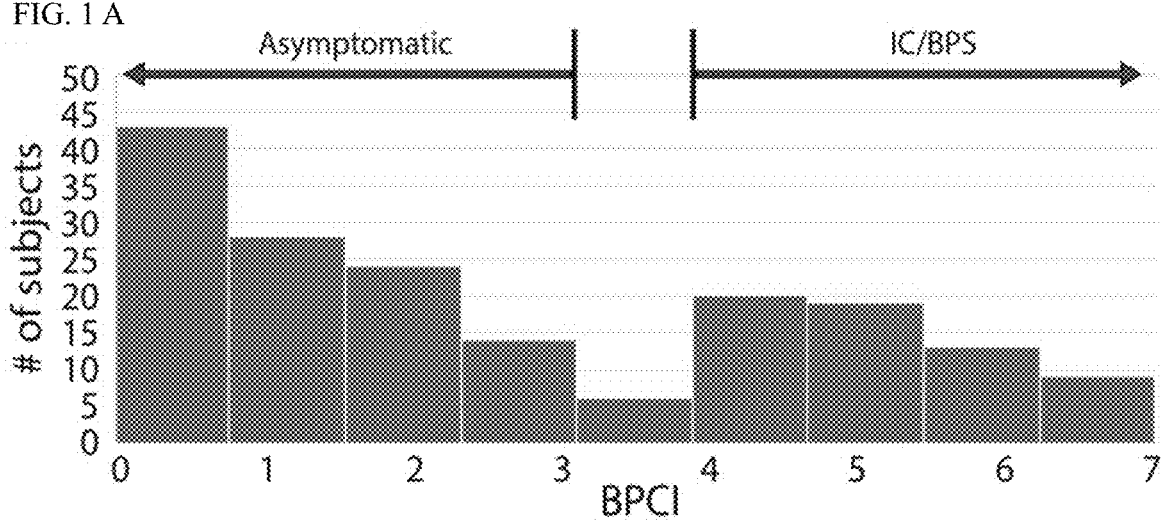
FIG. 1A-1B shows Bladder pain composite index (BPCI) defines more homogeneous IC/BPS and control populations. (1A) BPCI score distributions for 200 subjects with urinary symptoms revealed a clear division between patients with and without bladder pain that we will use to define our study populations for this proposal. (1B) Use of clinical diagnosis of IC/BPS results in substantial symptomatic overlap in bladder pain severity with controls (left), while separation based on a BPCI>4 provides homogeneous, distinct populations (right).
Figure 1:
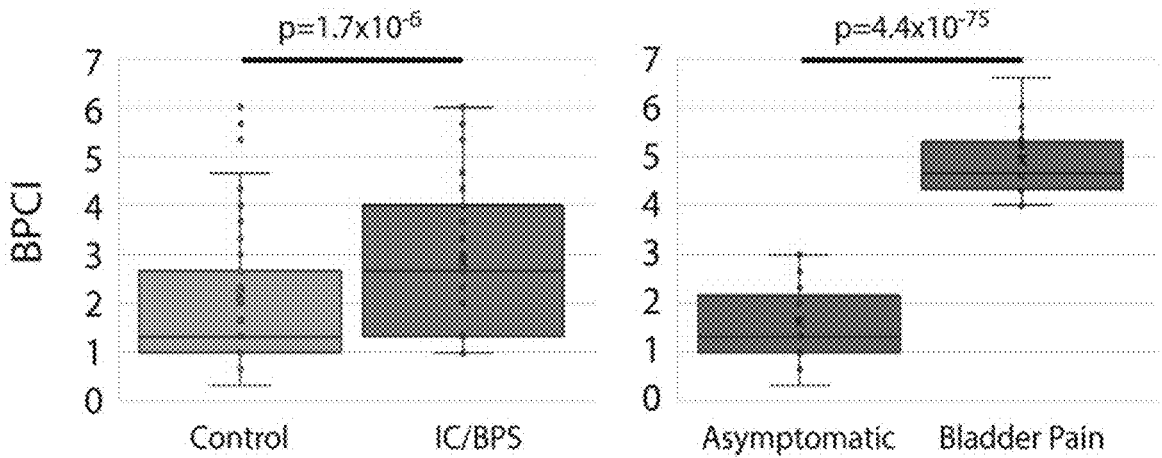

All references cited herein are incorporated by reference in their entirety as though fully set forth. Unless defined otherwise, technical and scientific terms used herein have the same meaning as commonly understood by one of ordinary skill in the art to which this invention belongs. Singleton et al., *Dictionary of Microbiology and Molecular Biology* 3$^{rd}$ ed., Revised, J. Wiley & Sons (New York, NY 2006); March, *Advanced Organic Chemistry Reactions, Mechanisms and Structure* 7$^{th}$ ed., J. Wiley & Sons (New York, NY 2013); and Sambrook and Russel, *Molecular Cloning: A Laboratory Manual* 4$^{th}$ ed., Cold Spring Harbor Laboratory Press (Cold Spring Harbor, NY 2012), provide one skilled in the art with a general guide to many of the terms used in the present application.

One skilled in the art will recognize many methods and materials similar or equivalent to those described herein, which could be used in the practice of the present invention. Indeed, the present invention is in no way limited to the methods and materials described. For purposes of the present invention, the following terms are defined below.

As used herein the term "about" when used in connection with a referenced numeric indication means the referenced numeric indication plus or minus up to 5% of that referenced numeric indication, unless otherwise specifically provided for herein. For example, the language "about 50%" covers the range of 45% to 55%. In various embodiments, the term "about" when used in connection with a referenced numeric indication can mean the referenced numeric indication plus or minus up to 4%, 3%, 2%, 1%, 0.5%, or 0.25% of that referenced numeric indication, if specifically provided for in the claims.

Given the substantial diagnostic confusion surrounding pelvic pain, we examined urinary bacterial associations with specific symptom clusters, not diagnoses. The present invention seeks to objectively identify subsets of bladder and pelvic pain as well as provide guidance as to the best possible treatment modalities for individuals.

Genitourinary bacteria appear to play a role in the development of chronic pain and genitourinary symptoms in female patients. The present invention reveals subtypes of bacterial colonization associated with different pain phenotypes and different responses to therapy. We describe herein the identification of clinically-useful bacterial biomarkers for specific pelvic and bladder pain phenotypes. Objective, rapid, and inexpensive testing to identify and classify reproductive-age women with bladder and pelvic pain would allow more accurate diagnosis and improve treatment decisions. The direct association of pathologic bacterial species concentration with severity of specific pain symptoms implicates a microbial role in the pathogenesis of genitourinary pain.

The identification of microbiota in the urinary tract has driven attempts to link bacterial species to a variety of urologic diseases. Multiple studies, however, have failed to find clear associations of bacterial taxa with an IC/BPS diagnosis. Using symptom-based patient classification, we defined unique bacterial community profiles for three distinct IC/BPS phenotypes, each associated with different inflammatory signatures. While previous reports have identified altered urinary microbiota and increased inflammatory mediators in IC/BPS, this is the first study to successfully integrate microbial, inflammatory, and symptomatic data into comprehensive IC/BPS phenotyping. Using larger numbers of patients within a more homogeneous age group, stringent inclusion criteria of both clinician diagnosis of IC/BPS and a validated symptomatic threshold ensured minimal cross-contamination and amplified differences between controls and symptomatic subjects to facilitate biomarker discovery.

A hurdle to interpreting investigations of urinary microbiota across centers has been the lack of relatability of datasets between sites; minor variations in protocols can result in large differences in taxal abundance. Using this phenotypic approach, consistent urotypes were identifiable using multiple NGS analytic pathways and verifiable using qPCR. We were able to establish qPCR-based concentration thresholds that accurately distinguished each phenotype. qPCR can provide rapid, inexpensive, and quantitative assessment of multiple species concurrently, making such an approach feasible for clinical use.

The disparate symptomatic and inflammatory features of each microbially-defined phenotype suggest distinct pathophysiologies. Symptomatically, the LI urotype most closely resembles classical IC/BPS, exhibiting bladder pain related to the voiding cycle. LI subjects exhibited increases in serum chemokines involved in mast cell chemotaxis and degranulation. Previous studies have observed similar elevations in urinary MCP-1, MDC and Eotaxin in IC/BPS subjects compared with controls, which can revert to normal after effective treatment with sacral neuromodulation. In mouse models of IC/BPS induced by MCP-1 overexpression, chemical irritation, LPS-stimulation, or autoimmune cystitis, elevated MCP-1 in the bladder promotes histamine release from bladder-resident mast cells, leading to bladder inflammation, reduced bladder capacity, and pelvic pain.

In contrast, urinary IL-17A and IL-22 were selectively suppressed in EC IC/BPS subjects. These cytokines are responsible for the clearance of extracellular bacteria and tissue repair at epithelial barrier surfaces. In mouse models, decreases in IL-22 result in increased epithelial damage and chronic bacterial colonization with uropathogenic *E. coli*. Neutralization of IL-17 at the onset of urinary *E. coli* infection leads to chronic bacterial cystitis in mice, when they would otherwise have resolved the infections. IL-15, which can antagonize IL-17A production, was elevated in EC subjects. GU *E. coli* infection can result in the type of pelvic pain seen in the NUPP group; our findings suggest decreases in IL-17 and IL-22 may inhibit tissue repair, impair epithelial barrier integrity, and promote chronic colonization with *E. coli* in EC IC/BPS subjects.

NIL IC/BPS subjects exhibit a phenotype unlikely to result from urinary microbial alterations, as no significant differences were found in either microbial taxa or associated inflammatory mediators. This phenotype exhibits urinary frequency, a sensation of incomplete emptying, aching and heaviness in the pelvis, and obstructive defecatory symptoms, as well as physical findings of pelvic floor myalgia, implicating myofascial pelvic pain referred to the bladder as the underlying etiology. The difficulties we experienced identifying specific symptoms solely associated with the MFP phenotype are likely explained by the fact that myofascial hypertonus is also frequently present in IC/BPS and other pain syndromes.

Given how different these phenotypes appear, we expect each will respond differently to treatment, perhaps explaining the low responder rates seen for most IC/BPS therapies. Objective biomarkers capable of classifying IC/BPS into clinically meaningful patient groups would transform IC/BPS management. In addition to enabling better clinical decision-making and earlier intervention for IC/BPS patients, it would empower a broader range of providers to initiate appropriate treatment. These markers have also begun to implicate inflammatory pathways altered in IC/BPS that could serve as targets for novel therapies. Pathologic microbial alterations in IC/BPS also suggest therapeutic strategies aimed at restoring healthy commensals. These results implicate microbially-driven visceral dysfunction in certain IC/BPS phenotypes.

We describe herein three distinct phenotypes of IC/BPS distinguishable by bacterial biomarkers. While all patient phenotypes perceived bladder-related pain, their associated symptomatic features and associated inflammatory signatures in blood and urine suggested distinct phenotypes resulting from unique etiologies. Detection of associated bacterial biomarkers using qPCR shows promise as an affordable, rapid, and objective method to identify these clinical phenotypes to improve the diagnosis and management of IC/BPS.

Various embodiments of the present invention are based, at least in part, on these findings.

Methods of Detecting

Various embodiments of the present invention provide for a method of detecting levels of one or more microorganisms in a subject in need thereof, comprising: assaying a biological sample obtained from the subject, wherein the subject has one or more symptoms of interstitial cystitis, pelvic pain or bladder pain; and detecting the levels of one or more microorganisms in the biological sample.

Various embodiments of the invention provide for a method of detecting levels of one or more microorganisms in a subject in need thereof, comprising: assaying a biological sample obtained from the subject, wherein the subject has one or more symptoms of interstitial cystitis, pelvic pain, bladder pain or myofascial pain; and detecting the levels of one or more microorganisms in the biological sample. In various embodiments, the myofascial pain is myofascial pelvic pain.

In various embodiments, the method comprises detecting the levels of 2, 3, 4, 5, 6, 7, 8, 9, 10 or more microorganisms in the biological sample. In various embodiments, the method comprises detecting the levels of 10, 15, 20, 25, 30, 35, 40, 45 or 50 or more microorganisms in the biological sample.

In various embodiments, the one or more microorganisms are *Lactobacillus* and Enterobacteriaceae bacteria. In various embodiments, the one or more microorganisms is *Lactobacillus iners* (*L. iners*). In various embodiments, the one or more microorganisms is *E. coli*. In various embodiments, the one or more microorganisms comprise *L. iners* and *E. coli*.

In various embodiments, the one or more organisms comprise non-*iners Lactobacilli* (NIL), *Lactobacillus iners*, Enterobacteriaceae, or *Shigella*. In various embodiments, the one or more microorganisms comprises non-*iners Lactobacilli* (NIL), *Lactobacillus iners* (*L. iners*), *E. coli*, or *Shigella*.

In various embodiments, the biological sample is urine. Additional examples of biological samples include but are not limited to body fluids, whole blood, plasma, serum, vaginal fluids or aspirate, stool, intestinal fluids or aspirate, and stomach fluids or aspirate, cerebral spinal fluid (CSF), sweat, saliva, cervical scraping, and mucous.

In various embodiments, the method further comprises comparing each detected level of the one or more microorganisms to each microorganism's reference level.

In some embodiments, the reference level can be established from biological samples from a healthy subject. For example, if the biological sample is urine, then the reference value can be obtained from the urine of a healthy subject. In other embodiments, the reference value is the average bacteria count for the same type of biological sample from a population of healthy subjects. In other embodiments, the reference value is the average plus one or two standard deviations of average methanogen count for the same type of biological sample from a population of healthy subjects. In some embodiments, the population of healthy subjects can range from at least three healthy individuals to 25 healthy individuals, more than 50 healthy individuals, and even more than 100 healthy individuals. A healthy individual is an individual who does not have interstitial cystitis, pelvic pain, bladder pain, or myofascial pain, or who does not have any symptoms of interstitial cystitis, pelvic pain, bladder pain, or myofascial pain.

Symptoms of interstitial cystitis include but are not limited to pain in the pelvis or between the vagina and anus in women, chronic pelvic pain, a persistent, urgent need to urinate, frequent urination, often of small amounts, throughout the day and night (e.g., up to 60 times a day), pain or discomfort while the bladder fills and relief after urinating, and pain during sexual intercourse. Symptoms of pelvic pain include but are not limited to pain or cramps before or during a menstrual period, pain during or after sex, pain during ovulation, painful bowel movements, rectal bleeding during a menstrual period, pain during urination, lower back pain, infertility, spotting between periods, and bloating in the abdomen. Symptoms of myofascial pain included but are not limited to pelvic pressure and heaviness.

In various embodiments, the subject is human. In various embodiments, the subject is female. In various embodiments, the subject does not have an active urinary tract infection as defined by a negative bacterial culture. That is, the subject, if tested would have a negative bacterial culture; for example, if the urine was cultured.

In various embodiments, the assay comprising using a technique selected from the group consisting of qPCR, RT-PCR, and next-generation sequencing.

In various embodiments of the present invention, *Lactobacillus iners* (*L. iners*) is detected by using a technique selected from the group consisting of qPCR, RT-PCR, and next-generation sequencing. In various embodiments of the present invention, *E. coli* is detected by using a technique selected from the group consisting of qPCR, RT-PCR, and next-generation sequencing. In various embodiments of the present invention, non-*iners Lactobacilli* is detected by using a technique selected from the group consisting of qPCR, RT-PCR, and next-generation sequencing. In various embodiments of the present invention, *shigella* is detected by using a technique selected from the group consisting of qPCR, RT-PCR, and next-generation sequencing.

Methods of Treatment

Various embodiments of the present invention provide for a method for treating interstitial cystitis, pelvic pain or bladder pain, comprising: administering a local bladder therapy to a subject who has been detected to have a level of *Lactobacillus iners* (*L. iners*) higher than a reference level.

Various embodiments of the present invention provide for a method for treating interstitial cystitis, pelvic pain or bladder pain, comprising: administering a non-local bladder therapy to a subject who has been detected to have a level of *E. coli* higher than a reference level.

Various embodiments of the present invention provide for a method for treating interstitial cystitis, pelvic pain, bladder pain or myofascial pain, comprising: administering a local bladder therapy to a subject who has been detected to have a level of *Lactobacillus iners* (*L. iners*) higher than a reference level.

Various embodiments of the present invention provide for a method for treating interstitial cystitis, pelvic pain, bladder pain, or myofascial pain, comprising: administering a non-local bladder therapy to a subject who has been detected to have a level of *E. coli* higher than a reference level.

Various embodiments of the present invention provide for a method for treating interstitial cystitis, pelvic pain, bladder pain, or myofascial pain, comprising: administering a musculoskeletal-directed therapy to a subject who has been detected to have both a level of *Lactobacillus iners* (*L. iners*) lower than a reference level, and a level of *E. coli* lower than a reference level.

Various embodiments of the present invention provide for a method for treating interstitial cystitis, pelvic pain or bladder pain in a subject, comprising: obtaining or requesting the results of an analysis of levels of one or more microorganisms in a biological sample obtained from the subject; and administering a local bladder therapy to a subject who has been detected to have a level of *Lactobacillus iners* (*L. iners*) higher than a reference level.

Various embodiments of the present invention provide for a method for treating interstitial cystitis, pelvic pain, bladder pain or myofascial pain in a subject, comprising: obtaining or requesting the results of an analysis of levels of one or more microorganisms in a biological sample obtained from the subject; and administering a local bladder therapy to a subject who has been detected to have a level of *Lactobacillus iners* (*L. iners*) higher than a reference level.

Various embodiments of the present invention provide for a method for treating interstitial cystitis, pelvic pain or bladder pain in a subject, comprising: obtaining or requesting the results of an analysis of levels of one or more microorganisms in a biological sample obtained from the subject; and administering a non-local bladder therapy to a subject who has been detected to have a level of *E. coli* higher than a reference level.

Various embodiments of the present invention provide for a method for treating interstitial cystitis, pelvic pain, bladder pain or myofascial pain in a subject, comprising: obtaining or requesting the results of an analysis of levels of one or more microorganisms in a biological sample obtained from the subject; and administering a non-local bladder therapy to a subject who has been detected to have a level of *E. coli* higher than a reference level.

Various embodiments of the present invention provide for a method for treating interstitial cystitis, pelvic pain, bladder pain or myofascial pain in a subject, comprising: obtaining or requesting the results of an analysis of levels of one or more microorganisms in a biological sample obtained from the subject; and administering a musculoskeletal-directed therapy to a subject who has been detected to have both a level of *Lactobacillus iners* (*L. iners*) lower than a reference level, and a level of *E. coli* lower than a reference level.

In various embodiments of the present invention, the local bladder therapy is a bladder instillation.

In various embodiments of the present invention, the bladder instillation comprises instilling an agent selected from the group consisting of alkalinized lidocaine and heparin, dimethyl sulfoxide (DMSO), sodium hyaluronate, heparin, a bladder cocktail, and an experimental solution.

In various embodiments of the present invention, the bladder cocktail comprises a combination selected from the group consisting of bupivacaine, heparin, hydrocortisone and sodium bicarbonate; bupivacaine, lidocaine jelly, triamcinolone, heparin, and gentamicin; lidocaine, sodium bicarbonate, heparin, and gentamicin; DMSO, heparin, triamcinolone, sodium bicarbonate, and gentamicin; heparin and bupivacaine; DMSO, hydrocortisone, bupivacaine, sodium bicarbonate, and optionally heparin.

In various embodiments of the present invention, the bladder cocktail comprises bupivacaine, heparin, hydrocortisone, sodium bicarbonate, lidocaine jelly, triamcinolone, gentamicin, lidocaine, gentamicin, DMSO, triamcinolone, or combinations thereof.

In various embodiments of the present invention, the experimental solution is selected from the group consisting of PSD597, URG101, URACYST (formulation of sterlie sodium chondroitin sulfate solution (2.0%)); LIPELLA liposomes, misoprostol, and combinations thereof.

PSD597 (PLETHORA SOLUTIONS) is a formulation of alkalinized lidocaine. It includes a delivery system and a proprietary formulation said to protect the active drug in the bladder and ensure that the drug remains in the optimal chemical form for transport across the bladder wall to its site of action. URG101 (URIGEN) is a formulation of alkalinized lidocaine and heparin for instillation. URACYST (STELLAR PHARMACEUTICALS) is a formulation of sterile sodium chondroitin sulfate solution (2.0%). LIPOSOMES FOR INSTILLATION (LIPELLA) (see e.g., Chuang Y C et al. J Urol. 2009; 182:1393-1400) is a treatment wherein liposomes are instilled once a week for four weeks. MISOPROSTOL (CYTOTEC) FOR INSTILLATION is a prostaglandin E1 analog.

In various embodiments, the musculoskeletal-directed therapy comprises myofascial release, guided pelvic floor physical therapy/pelvic floor myofascial rehabilitation, or both.

In various embodiments of the present invention, the biological sample is urine. Additional examples of biological samples are as provided herein.

In various embodiments, the subject is human. In various embodiments, the subject is female. In various embodiments of the present invention, the subject does not have an active urinary tract infection as defined by a negative bacterial culture.

In various embodiments of the present invention, *Lactobacillus iners* (*L. iners*) is detected by using a technique selected from the group consisting of qPCR, RT-PCR, and next-generation sequencing. In various embodiments of the present invention, *E. coli* is detected by using a technique selected from the group consisting of qPCR, RT-PCR, and next-generation sequencing. In various embodiments of the present invention, non-*iners Lactobacilli* is detected by using a technique selected from the group consisting of qPCR, RT-PCR, and next-generation sequencing. In various embodiments of the present invention, *shigella* is detected by using a technique selected from the group consisting of qPCR, RT-PCR, and next-generation sequencing.

In various embodiments detection of *L. iners, E. coli, non-iners Lactobacilli, shigella*, or any combination thereof comprises using a method of detecting levels of one or more microorganisms as described herein.

Methods of Selection

Various embodiments of the present invention provide for a method of selecting a treatment for a subject having interstitial cystitis, pelvic pain or bladder pain, comprising detecting levels of one or more microorganisms in a biological sample obtained from a subject in need thereof, selecting local bladder treatment for subjects with levels of *Lactobacillus iners* (*L. iners*) that are higher than a reference level indicates a local bladder treatment for the subject, or selecting a non-local bladder treatment for subjects with levels of Enterobacteriaceae bacteria that are higher than a reference level indicates based on the understanding that the subject will be refractory to local bladder therapies.

Various embodiments of the present invention provide for a method of selecting a treatment for a subject having interstitial cystitis, pelvic pain, bladder pain, or myofascial pain, comprising detecting levels of one or more microorganisms in a biological sample obtained from a subject in need thereof, selecting local bladder treatment for subjects with levels of *Lactobacillus iners* (*L. iners*) that are higher than a reference level indicates a local bladder treatment for the subject, or selecting a non-local bladder treatment for subjects with levels of Enterobacteriaceae bacteria that are higher than a reference level indicates based on the understanding that the subject will be refractory to local bladder therapies, or selecting a musculoskeletal-directed therapy to a subject who has been detected to have both a level of *Lactobacillus iners* (*L. iners*) lower than a reference level, and a level of *E. coli* lower than a reference level based on the understanding that the subject will be refractory to local bladder therapies.

In various embodiments of the present invention, the local bladder therapy is a bladder instillation.

In various embodiments of the present invention, the bladder instillation comprises instilling an agent selected from the group consisting of alkalinized lidocaine and heparin, dimethyl sulfoxide (DMSO), sodium hyaluronate, heparin, a bladder cocktail, and an experimental solution.

In various embodiments of the present invention, the bladder cocktail comprises a combination selected from the group consisting of bupivacaine, heparin, hydrocortisone and sodium bicarbonate; bupivacaine, lidocaine jelly, triamcinolone, heparin, and gentamicin; lidocaine, sodium bicarbonate, heparin, and gentamicin; DMSO, heparin, triamcinolone, sodium bicarbonate, and gentamicin; heparin and bupivacaine; DMSO, hydrocortisone, bupivacaine, sodium bicarbonate, and optionally heparin.

In various embodiments of the present invention, the bladder cocktail comprises bupivacaine, heparin, hydrocortisone, sodium bicarbonate, lidocaine jelly, triamcinolone, gentamicin, lidocaine, gentamicin, DMSO, triamcinolone, or combinations thereof.

In various embodiments of the present invention, the experimental solution is selected from the group consisting of PSD597, URG101, URACYST (formulation of sterlie sodium chondroitin sulfate solution (2.0%)); LIPELLA liposomes, misoprostol, and combinations thereof.

PSD597 (PLETHORA SOLUTIONS) is a formulation of alkalinized lidocaine. It includes a delivery system and a proprietary formulation said to protect the active drug in the bladder and ensure that the drug remains in the optimal chemical form for transport across the bladder wall to its site of action. URG101 (URIGEN) is a formulation of alkalinized lidocaine and heparin for instillation. URACYST (STELLAR PHARMACEUTICALS) is a formulation of sterile sodium chondroitin sulfate solution (2.0%). LIPOSOMES FOR INSTILLATION (LIPELLA) (see e.g., Chuang Y C et al. J Urol. 2009; 182:1393-1400) is a treatment wherein liposomes are instilled once a week for four weeks. MISOPROSTOL (CYTOTEC) FOR INSTILLATION is a prostaglandin E1 analog.

In various embodiments, the musculoskeletal-directed therapy comprises myofascial release, guided pelvic floor physical therapy/pelvic floor myofascial rehabilitation, or both.

In various embodiments of the present invention, the biological sample is urine. Additional examples of biological samples are as provided herein.

In various embodiments, the subject is human. In various embodiments, the subject is female. In various embodiments of the present invention, the subject does not have an active urinary tract infection as defined by a negative bacterial culture.

In various embodiments of the present invention, *Lactobacillus iners* (*L. iners*) is detected by using a technique selected from the group consisting of qPCR, RT-PCR, and next-generation sequencing. In various embodiments of the present invention, *E. coli* is detected by using a technique selected from the group consisting of qPCR, RT-PCR, and next-generation sequencing. In various embodiments of the present invention, non-*iners Lactobacilli* is detected by using a technique selected from the group consisting of qPCR, RT-PCR, and next-generation sequencing. In various embodiments of the present invention, *shigella* is detected by using a technique selected from the group consisting of qPCR, RT-PCR, and next-generation sequencing.

Methods of Identifying Bacterial Phenotype

Various embodiments of the present invention provide for identifying a bacterial phenotype in a subject in need thereof, comprising: detecting levels of one or more microorganisms in a biological sample obtained from a subject in need thereof; and identifying the subject as a non-*iners Lactobacilli* phenotype if both a level of *Lactobacillus iners* (*L. iners*) is lower than its reference level, and a level of *E. coli* lower is than its reference level, identifying the subject as a *Lactobacillus iners* phenotype if the levels of *Lactobacillus iners* is higher than a reference level for *Lactobacillus iners*, or identifying the subject as a *Escherichia/Shigella* phenotype if the levels of *Escherichia, Shigella*, or both are higher than reference levels for *Escherichia* and *Shigella*. Bacterial phenotype is also referred herein as urotype.

In various embodiments, the subject has one or more symptoms of interstitial cystitis, pelvic pain, bladder pain, or myofascial pain.

In various embodiments, the method further comprises treating the subject based on the identified bacterial phenotype. In various embodiments, a local bladder treatment is administered for subjects with levels of *Lactobacillus iners* (*L. iners*) that are higher than a reference level. In various embodiments, musculoskeletal-directed therapy is administered for subjects with both a level of *Lactobacillus iners* (*L. iners*) lower than a reference level and a level of *E. coli* lower than a reference level.

In various embodiments of the present invention, the local bladder therapy is a bladder instillation.

In various embodiments of the present invention, the bladder instillation comprises instilling an agent selected from the group consisting of alkalinized lidocaine and heparin, dimethyl sulfoxide (DMSO), sodium hyaluronate, heparin, a bladder cocktail, and an experimental solution.

In various embodiments of the present invention, the bladder cocktail comprises a combination selected from the group consisting of bupivacaine, heparin, hydrocortisone and sodium bicarbonate; bupivacaine, lidocaine jelly, triamcinolone, heparin, and gentamicin; lidocaine, sodium bicarbonate, heparin, and gentamicin; DMSO, heparin, triamcinolone, sodium bicarbonate, and gentamicin; heparin and bupivacaine; DMSO, hydrocortisone, bupivacaine, sodium bicarbonate, and optionally heparin.

In various embodiments of the present invention, the bladder cocktail comprises bupivacaine, heparin, hydrocortisone, sodium bicarbonate, lidocaine jelly, triamcinolone, gentamicin, lidocaine, gentamicin, DMSO, triamcinolone, or combinations thereof.

In various embodiments of the present invention, the experimental solution is selected from the group consisting of PSD597, URG101, URACYST (formulation of sterlie sodium chondroitin sulfate solution (2.0%)); LIPELLA liposomes, misoprostol, and combinations thereof.

PSD597 (PLETHORA SOLUTIONS) is a formulation of alkalinized lidocaine. It includes a delivery system and a proprietary formulation said to protect the active drug in the bladder and ensure that the drug remains in the optimal chemical form for transport across the bladder wall to its site of action. URG101 (URIGEN) is a formulation of alkalinized lidocaine and heparin for instillation. URACYST (STELLAR PHARMACEUTICALS) is a formulation of sterile sodium chondroitin sulfate solution (2.0%). LIPOSOMES FOR INSTILLATION (LIPELLA) (see e.g., Chuang Y C et al. J Urol. 2009; 182:1393-1400) is a treatment wherein liposomes are instilled once a week for four weeks. MISOPROSTOL (CYTOTEC) FOR INSTILLATION is a prostaglandin E1 analog.

In various embodiments, the musculoskeletal-directed therapy comprises myofascial release, guided pelvic floor physical therapy/pelvic floor myofascial rehabilitation, or both.

In various embodiments of the present invention, the biological sample is urine. Additional examples of biological samples are as provided herein.

In various embodiments, the subject is human. In various embodiments, the subject is female. In various embodiments of the present invention, the subject does not have an active urinary tract infection as defined by a negative bacterial culture.

In various embodiments of the present invention, *Lactobacillus iners* (*L. iners*) is detected by using a technique selected from the group consisting of qPCR, RT-PCR, and next-generation sequencing. In various embodiments of the present invention, *E. coli* is detected by using a technique selected from the group consisting of qPCR, RT-PCR, and next-generation sequencing. In various embodiments of the present invention, non-*iners Lactobacilli* is detected by using a technique selected from the group consisting of qPCR, RT-PCR, and next-generation sequencing. In various embodiments of the present invention, *shigella* is detected by using a technique selected from the group consisting of qPCR, RT-PCR, and next-generation sequencing.

Kits

Various embodiments of the present invention provide for an assay kit to identify a bacterial phenotype in a subject in need thereof, comprising: one or more labeled probes for detecting one or more microorganisms; one or more primers, each capable of specifically binding to each of the one or more microorganisms in a biological sample obtained from a subject in need thereof; and DNA polymerase. In various embodiments, DNA polymerase is Taq DNA polymerase. In various embodiments, the assay further comprises a buffer.

In various embodiments, the subject has one or more symptoms of interstitial cystitis, pelvic pain, bladder pain or myofascial pain.

In various embodiments, the one or more labeled probes are specific for one or more of non-*iners Lactobacilli*, *Lactobacillus iners, Escherichia*, or *Shigella*. In various embodiments, the labeled probe is specific for *E. coli*.

In various embodiments, the one or more primers are each specific for each of one or more of non-*iners Lactobacilli, Lactobacillus iners, Escherichia*, or *Shigella*. In various embodiments, the primer is specific for *E. coli*. In various embodiments, the primers are selected from Table 1.

As used herein, the term "label" refers to a composition capable of producing a detectable signal indicative of the presence of a target. Suitable labels include fluorescent molecules, radioisotopes, nucleotide chromophores, enzymes, substrates, chemiluminescent moieties, magnetic particles, bioluminescent moieties, and the like. As such, a label is any composition detectable by spectroscopic, photochemical, biochemical, immunochemical, electrical, optical or chemical means needed for the methods and devices described herein. For example, the peptides can be labeled with a detectable tag which can be detected using an antibody specific to the label.

The exact nature of the components configured in the assay kit depends on its intended purpose. In one embodiment, the kit is configured particularly for the purpose of diagnosing or classifying mammalian subjects. In another embodiment, the kit is configured particularly for the purpose of diagnosing or classifying human subjects. In further embodiments, the kit is configured for veterinary applications, treating subjects such as, but not limited to, farm animals, domestic animals, and laboratory animals.

Instructions for use may be included in the kit. "Instructions for use" typically include a tangible expression describing the technique to be employed in using the components of the kit to effect a desired outcome, such as to diagnose or classifying the phenotype of the subject in need thereof. Optionally, the kit also contains other useful components, such as, containers, diluents, buffers, pharmaceutically acceptable carriers, syringes, catheters, applicators, pipetting or measuring tools, bandaging materials or other useful paraphernalia as will be readily recognized by those of skill in the art.

The materials or components assembled in the kit can be provided to the practitioner stored in any convenient and suitable way that preserves their operability and utility. For example, the components can be in dissolved, dehydrated, or lyophilized form; they can be provided at room, refrigerated or frozen temperatures. The components are typically contained in suitable packaging material(s). As employed herein, the phrase "packaging material" refers to one or more physical structures used to house the contents of the kit, such as inventive compositions and the like. The packaging material is constructed preferably to provide a sterile, contaminant-free environment. The packaging materials employed in the kit are those customarily utilized in qPCR purposes. As used herein, the term "package" refers to a suitable solid matrix or material such as glass, plastic, paper, foil, and the like, capable of holding the individual kit components. Thus, for example, a package can be a glass vial used to contain suitable quantities of the labeled probes. The packaging material generally has an external label which indicates the contents and/or purpose of the kit and/or its components.

EXAMPLES

The following examples are provided to better illustrate the claimed invention and are not to be interpreted as limiting the scope of the invention. To the extent that specific materials are mentioned, it is merely for purposes of illus-

Example 1

Methods: Catheterized urinary samples were obtained from 78 pre-menopausal women (age 18-45) with a variety of urinary complaints, including bladder and pelvic pain. 16S next-generation sequencing (NGS) was used to characterize urinary microbial populations; validated questionnaires (female GenitoUrinary Pain Index, OAB questionnaire, O'Leary-Sant Indices) were used to quantify symptom type and severity. K means unsupervised clustering analysis of NGS data was used to assign subjects to urotypes, based on the urinary bacterial community composition. Quantitative PCR (qPCR) served to confirm the NGS results and provide objective concentrations for taxa of interest. Linear regression analysis confirmed the associations of bacterial concentrations and specific symptoms.

Results: In an exploratory population of 35 reproductive-age women with a variety of complaints, 16S NGS revealed four urotypes that strongly correlated with symptomatology. Isolated urgency incontinence was rare; the majority of subjects with symptoms complained of genitourinary pain. Bladder-specific pain (worse with filling, relieved by voiding) was strongly associated with *Lactobacillus iners*, a *Lactobacillus* spp. that does not produce lactic acid. Asymptomatic patients almost universally had a non-*iners Lactobacillus*-predominant microbiota. Vaginal and urethral pain unrelated to voiding was positively correlated with increasing Enterobacteriaceae, confirmed on qPCR to be primarily *Escherichia coli*. Detection of these two pathobiont species by qPCR in a second validation population (n=43) was highly predictive of each phenotype (P<0.00001).

Retrospective chart review indicated that only the *L. iners*-associated population responded to local bladder therapies, such as bladder instillations. Objective, rapid, and scalable testing to classify bladder and pelvic pain appropriately would allow more accurate diagnosis and improve treatment. The rising pain levels seen in association with increasing pathogenic bacterial abundance suggests a possible role for these taxa in pain physiology.

Example 2

Participants

After IRB approval (Pro00046154), 84 pre-menopausal women (aged 18-45) were recruited. IC/BPS subjects were diagnosed by a board-certified FPMRS specialist according to AUA Guidelines. Controls denied any urinary complaints and had asymptomatic scores on all questionnaires. Exclusion criteria included active urinary tract infection, prior pelvic surgery, pregnancy, diabetes, neurologic or rheumatic disease (e.g. multiple sclerosis), spinal cord injury, current smoking, a vaginal pessary, cyclic pain at menses, immunomodulatory medication use, and urinary tract instrumentation or antibiotic administration within the past 6 weeks. While these are exclusion criteria for this study described herein, they do not necessarily exclude these patient populations from the scope of the claims unless specifically specified by the claims; for example, if each and any of these populations of person are specifically disclaimed in the claims.

All patients completed the female GenitoUrinary Pain Index (fGUPI), overactive bladder questionnaire (OABq), Pelvic Floor Distress Inventory (PFDI)-20, Incontinence Impact Questionnaire (IIQ-7), and Interstitial Cystitis Symptom and Problem Indices (ICSI/ICPI) to measure symptom type and severity. Baseline demographics and clinical data, including age, body mass index (BMI), co-morbid conditions, past surgeries, and medication usage, including hormonal medications, were captured at enrollment.

Sample Collection and DNA Extraction

Catheterized urine samples were obtained after sterile preparation of the urethra. Urine specimens were processed as described using a sample processing methodology optimized for microbial analysis of catheterized urine samples. Bacterial content was assessed by quantitative Polymerase Chain Reaction (qPCR) using broad specificity eubacterial primers.

TABLE 1

Bacterial Primers for PCR amplification

| Amplicon | Forward | SEQ ID NO: | Reverse | SEQ ID NO: |
|---|---|---|---|---|
| 16S (8F&R357) | 5'-AGAGTTTGATCMTGGCTC AG-3' | 1 | 5'-CTGCTGCCTYCCGTA-3' | 2 |
| Eubacteria | 5'-ACTCCTACGGGAGGCAG CAGT-3' | 3 | 5'-ATTACCGCGGCTGCTGGC-3' | 4 |
| E. coli | 5'-GGAAGAAGCTTGCTTCTT TGCTGAC-3' | 5 | 5'-AGCCCGGGGATTTCACATCTGA CTTA-3' | 6 |
| L. iners | 5'-GTCTGCCTTGAAGATCGG -3' | 7 | 5'-ACAGTTGATAGGCATCATC-3' | 8 |

Next-Generation Sequencing

Bacterial 16S region sequences were generated by PCR from 1 ng sample DNA using the 8F and R357 primers as described. A mock community dilution series and each of the DNA isolation reagents were evaluated in parallel in all sequencing runs to identify contaminants and significant batch variations. For taxonomic assignment, the pilot population was analyzed with an operational taxonomic unit (OTU) approach using the UCLUST algorithm of QIIME in combination with the GreenGenes database, while the validation population utilized an amplicon sequence variants (ASV) approach using the DADA2 algorithm in combination with the Silva bacterial ribosomal RNA sequence database (release 132) at 99% identity.

Real Time qPCR to Quantify Urinary Bacterial DNA qPCR used 10 nM species-specific primers for *E. coli* and *L. iners* in combination with 2 ml template DNA and SYBR Green PCR kit (Applied Biosystems) in a qTower3 G thermal cycler (Analytik Jena). Standard curves were created using serial dilutions of DNA isolated from purified cultures of each species (American Type Culture Collection). To verify accuracy, qPCR products were analyzed by 2% agarose gel electrophoresis to confirm anticipated product size. Relative quantities of taxal DNAs were calculated by comparative CT method (2-ΔΔCT method) and normalized to standards consistent across experiments. Bivariate microbial differences between IC/BPS clusters were examined using either parametric Welch t test or non-parametric Mann-Whitney test. Assay accuracy for the IC/BPS phenotyping by qPCR was evaluated using multinomial logistic regression models. Nonparametric ROC analysis determined symptomatic thresholds for qPCR testing.

Inflammatory Biomarker Analysis

The concentrations of 40 cytokines, chemokines, and growth factors in serum and urine samples from IC/BPS subjects and healthy controls were analyzed using V-PLEX electrochemiluminescent detection (Meso Scale Diagnostics).

Statistical Analysis

Differences in characteristics between groups (IC/BPS vs. controls) were evaluated using t-tests for continuous variables. The Mann-Whitney U test made pairwise comparisons between symptomatic and inflammatory features of urotypes. Multiple regression analysis determined relative associations; Pearson's correlation coefficients were calculated to determine the correlations between microbial abundance and symptomatic features. P values less than ≤0.05 were considered significant. All data analyses were performed in R Studio (v1.2.1335).

Exploratory visualizations of microbiome data were performed with phyloseq (version 1.14.0) using relative abundances after removing very low abundance OTUs. Beta diversity was assessed by weighted UniFrac distance matrices and visualized by principal coordinate analysis using QIIME2 (2020.2).

To identify urotypes, we used k-means clustering to classify IC/BPS subjects using NGS data. The number of clusters was determined using an information theoretic approach. A random forest classifier[51] determined individual patient-reported measures associated with specific urotypes. Linear discriminant analysis (LDA) effect size (LEfSe) identified statistically significant differences in the relative abundance of taxa associated with IC/BPS. Taxa with LEfSe>4 were considered significantly enriched.

To identify symptom-associated microbial alterations, we used the MaAsLin method to discover associations between clinical metadata and microbial abundance. The false discovery rate (FDR) was controlled by Benjamini-Hochberg procedure. The multivariate association analysis was conducted with minimum OTU prevalence of 0.05, minimum abundance of 0.2%, and FDR-corrected p-value cutoff of 0.10.

Objective Symptom Measures Provide Better Identification of IC/BPS Patients than Clinician Diagnosis As no objective diagnostic criteria exist for IC/BPS, this study defined IC/BPS population with the combination of FPMRS subspecialist diagnosis and an objective symptomatic threshold: the Bladder Pain Composite Index (BPCI) (FIG. 1A). BPCI use distinguishes a homogeneous population with bladder-related pain from controls and excludes both mild cases and pain unrelated to the bladder (FIG. 1B).

Figure 2:
FIG. 2 shows microbial patterns are associated with bladder-related pain subtypes in pre-menopausal women. Urinary bacterial composition for 35 pre-menopausal women with and without bladder pain are shown as stacked bar plots. Pain scores for each subject on an 11-point Likert scale are shown in the heat bar below the graphs. Subject bacterial composition was classified into three unique "urotypes" (see color bar above graph), characterized by the presence of primarily non-*iners* Lactobacilli (NIL, orange), *Lactobacillus iners* (LI, purple), or *Escherichia/Shigella* (EC, blue).

Identification of Symptom-Specific Urinary Microbial Profiles Associated with Bladder and Pelvic Pain To identify relevant microbial biomarkers that correlate with IC/BPS, catheterized urine samples were obtained from a pilot population of 35 (24 IC/BPS and 11 controls) age-matched, pre-menopausal women. 16S V2-V3 NGS revealed three distinct urinary bacterial community states (FIG. 2), known as "urotypes". K-means clustering of NGS data objectively confirmed this classification; each urotype had a characteristic community distinguishable by a different bacterial taxon: non-*iners* Lactobacilli (NIL), *Lactobacillus iners* (LI), or *Escherichia/Shigella*, which includes *Escherichia coli* (EC). The NIL and LI groups were nearly identical in composition, differing only in the absence or presence of LI, while the EC group was more diverse.

Bacterial Urotypes Correlate with Symptomatic Patterns

To correlate these urotypes with distinct clinical phenotypes, we examined subjects' symptomatic complaints on multiple questionnaires examining GU symptomatology. The LI urotype demonstrated increased bladder pain symptoms (BPS), in which bladder-specific pain (ICSI4) was worse with bladder filling (GUPI2c) and relieved by bladder emptying (GUPI2d). The EC urotype was associated with non-urologic pelvic pain (NUPP) characterized by global pelvic pain (GUPI1d) unrelieved by bladder emptying (GUPI2d) and co-incident urethral (GUPI1c) and vaginal (GUPI1a,b) pain and dyspareunia (GUPI2b). The majority of asymptomatic patients (7/11) exhibited the NIL urotype. A few IC/BPS patients (3/24) possessed the NIL urotype and were indistinguishable by bacterial composition from controls, suggesting a third IC/BPS phenotype unrelated to microbial alterations.

Validation of Urotype Classification in a Secondary Patient Population

To validate this presumptive urotype-based classification, we recruited a second subset of 49 premenopausal IC/BPS patients. To ensure generalizability of our presumptive microbial classification, urinary bacterial communities in these patients were assessed by NGS using a different sequencing facility and analytical pipeline for taxonomic assignment. Overall, the different approach resulted in some changes in taxonomic assignment and global reductions in LI and EC abundances, these taxa remained clearly associated with each urotype (FIG. 3A). Moreover, the associations of LI and EC relative abundance with BPS and NUPP, respectively, were dose-dependent and highly significant (p<0.00001), even in this small population (FIG. 3B).

Symptomatic Patterns Associated with Urotypes Define Distinct IC/BPS Phenotypes

Figure 4A:
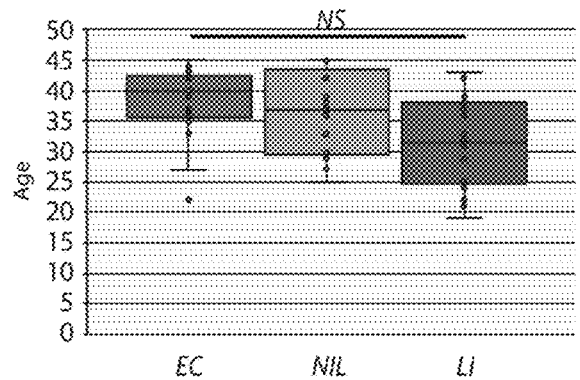
FIG. 4A-4F shows clinical features of IC/BPS patients by urotype. Urotypes were defined as *L. iners* (LI; purple), then any *Escherichia* (EC; blue) or other non-*iners* Lactobacilli (NIL; orange). The indicated clinical features were plotted as box and whisker plots. The EC group demonstrated the highest non-urologic pelvic pain, defined as the sum of GUPI1a-d and GUPI2b (4B). LI was homogenously high for isolated bladder pain (weighted sum of ICSI4, ICPI4, and GUPI2c) (4D) Increased myofascial pain (weighted sum of PFDI-20q2,5,7,12) was most pronounced in the NIL urotype. There were no significant differences in age (4A), the severity of urgency incontinence (4E), or symptomatic bother (4F). NS: Not Significant.
Figure 4C:
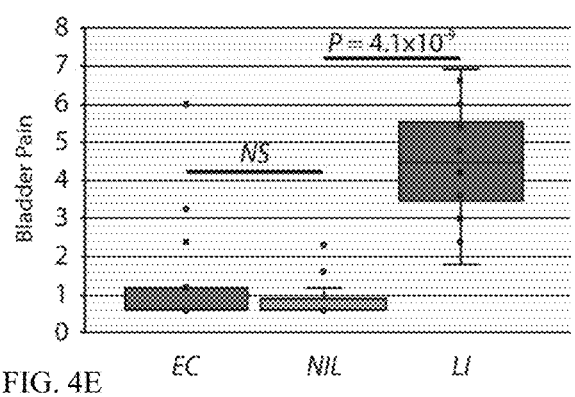
Figure 4E:
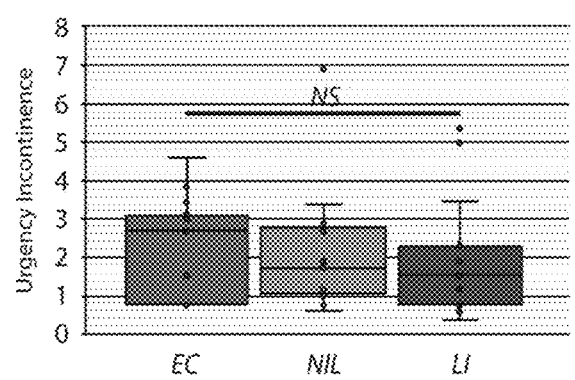
Figure 4B:
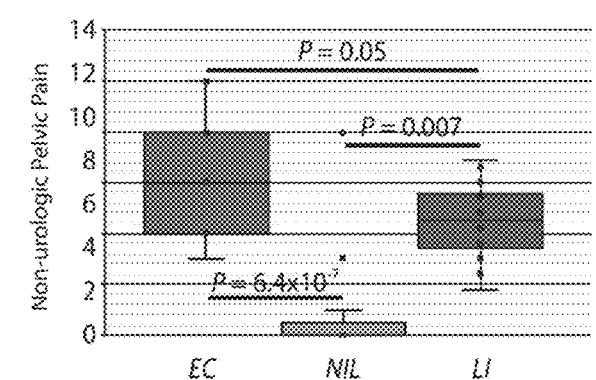
Figure 4D:
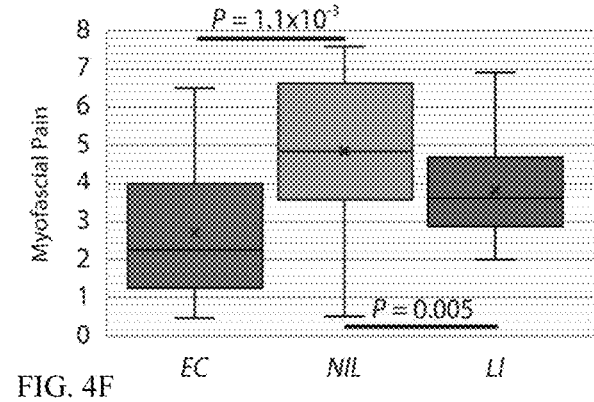
Figure 4F:
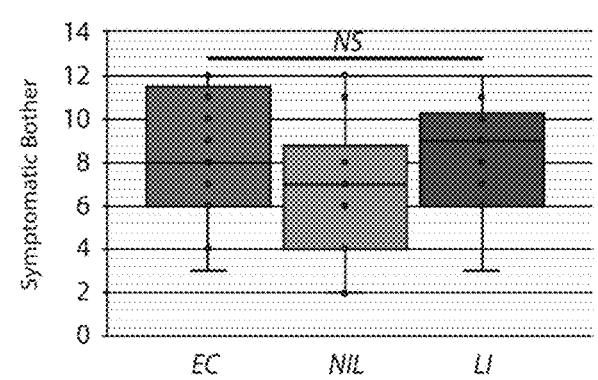

Subjects were divided into urotypes based on relative abundance, with subjects bearing *L. iners*>0.2% classified as LI and remaining subjects exhibiting *Escherichia*>0.2% classified as EC. The residual subjects exhibited >50% NIL (range: 52.4-89.8%, median 70.8%). All groups exhibited elevated bother scores and bothersome urinary complaints (Table 2). The EC group exhibited significantly higher levels than the other urotypes of NUPP features, encompassing vaginal (GUPI1a, p<0.05 GUPI1b, p<0.005) and urethral (GUPI1c, p<0.005) pain (FIG. 4B). The LI group exhibited statistically higher BPS, combining bladder-specific pain (ICSI4, p=0.05; ICPI4, p=0.02) and pain with bladder filling (GUPI2c, p=0.04) (FIG. 4C). The NIL IC/BPS subjects exhibited milder symptoms overall. While no individual symptom was significantly worse than in the other urotypes, NIL IC/BPS subjects exhibited most severe pain with bowel movements (PFDI-20q12, p=0.002 vs. LI), straining to defecate (PFDI-20 q7), pelvic heaviness (PFDI-20q2), and a sensation of incomplete emptying (PFDI-20q5). While none of these items reached statistical significance, when combined, this constellation of myofascial pain (MFP) features was significantly associated with NIL IC/BPS (p<0.005) (FIG. 4D).

TABLE 2

| Question | Symptom feature | NIL (Std Dev) | LI (Std Dev) | EC (Std. Dev) | P (NIL vs. LI) | P (NIL vs. EC) | P (LI vs EC) |
|---|---|---|---|---|---|---|---|
| IIQ7_1 | Symptoms affecting ability to do chores | 0.60 (±0.89) | 0.50 (±1.09) | 0.63 (±1.15) | 0.86 | 0.97 | 0.76 |
| IIQ7_2 | Symptoms affecting physical recreation | 1.00 (±1.41) | 1.29 (±1.20) | 0.94 (±1.18) | 0.69 | 0.93 | 0.43 |
| IIQ7_3 | Symptoms affecting entertainment | 1.40 (±1.34) | 0.86 (±1.17) | 0.81 (±1.22) | 0.40 | 0.37 | 0.92 |
| IIQ7_4 | Symptoms affecting travel away from home | 1.40 (±1.34) | 1.36 (±1.39) | 0.87 (±1.36) | 0.95 | 0.46 | 0.35 |
| IIQ7_5 | Symptoms affecting social participation | 0.80 (±1.30) | 1.21 (±1.31) | 0.75 (±1.24) | 0.55 | 0.94 | 0.33 |
| IIQ7_6 | Symptoms affecting emotional health | 0.60 (±1.34) | 1.36 (±1.22) | 0.88 (±1.20) | 0.26 | 0.67 | 0.29 |
| IIQ7_7 | Symptoms making you frustrated | 1.20 (±1.64) | 1.77 (±1.36) | 0.94 (±1.29) | 0.46 | 0.71 | 0.10 |
| IIQ7 Total | IIQ-7 1-7 | 2.62 (±5.97) | 6.05 (±7.36) | 5.41 (±7.55) | 0.17 | 0.28 | 0.80 |
| ICSI1 | Strong need to void with no warning | 2.00 (±2.13) | 2.89 (±1.57) | 1.88 (±1.75) | 0.20 | 0.87 | 0.08 |
| ICSI2 | Urinary frequency within 2 hours | 3.08 (±1.93) | 3.94 (±0.80) | 3.63 (±1.78) | 0.10 | 0.45 | 0.50 |
| ICSI3 | Nighttime urination | 1.58 (±1.62) | 1.97 (±1.46) | 2.13 (±1.45) | 0.50 | 0.36 | 0.76 |
| ICSI4 | Pain or burning in the bladder | 0.75 (±1.29) | 1.89 (±1.60) | 0.88 (±0.96) | *0.05* | 0.77 | *0.04* |
| ICSI Total | ICSI 1-4 | 6.85 (±6.23) | 10.13 (±4.29) | 8.00 (±4.77) | 0.09 | 0.57 | 0.17 |
| ICPI1 | Frequent daytime urination | 2.33 (±1.72) | 2.94 (±1.03) | 2.50 (±1.51) | 0.24 | 0.79 | 0.33 |
| ICPI2 | Getting up at night to urinate | 1.50 (±1.78) | 2.22 (±1.17) | 1.94 (±1.44) | 0.19 | 0.48 | 0.53 |
| ICPI3 | Need to urinate with little warning | 1.50 (±1.88) | 2.18 (±1.55) | 1.40 (±1.50) | 0.30 | 0.88 | 0.16 |
| ICPI4 | Bladder burning, pain, discomfort, or pressure | 1.75 (±1.54) | 2.94 (±1.14) | 1.73 (±1.71) | *0.02* | 0.98 | *0.02* |
| ICPI Total | ICPI 1-4 | 6.54 (±6.28) | 9.32 (±4.16) | 6.94 (±4.81) | 0.14 | 0.84 | 0.12 |
| OLS | ICSI + ICPI | 13.38 (±12.43) | 19.45 (±8.04) | 14.94 (±9.40) | 0.10 | 0.70 | 0.13 |
| OABq2 | Uncomfortable urge to urinate | 3.17 (±2.21) | 4.50 (±1.38) | 3.50 (±2.19) | 0.05 | 0.69 | 0.12 |
| OABq3 | Sudden urge to urinate with no warning | 2.75 (±2.42) | 3.33 (±1.91) | 2.94 (±1.98) | 0.47 | 0.82 | 0.56 |
| OABq4 | Accidental loss of small amounts of urine | 2.58 (±1.83) | 2.59 (±1.80) | 2.56 (±1.97) | 0.99 | 0.98 | 0.97 |
| OABq5 | Nighttime urination | 2.90 (±1.91) | 3.29 (±1.65) | 3.25 (±2.11) | 0.58 | 0.67 | 0.95 |
| OABq6 | Waking at night to urinate | 2.92 (±1.78) | 3.44 (±1.58) | 3.75 (±1.84) | 0.40 | 0.24 | 0.61 |
| OABq8 | Urine loss associated with strong urgency | 2.36 (±2.01) | 2.39 (±1.82) | 1.93 (±1.49) | 0.97 | 0.54 | 0.44 |
| OABq SF | OABq 2-6, 8 | 17.15 (±11.55) | 19.47 (±9.10) | 16.76 (±9.51) | 0.53 | 0.92 | 0.39 |
| GUPI1A | Discomfort at the entrance to the vagina | 0.27 (±0.47) | 0.24 (±0.44) | 0.67 (±0.49) | 0.83 | *0.05* | *0.01* |
| GUPI1B | Discomfort in the vagina | 0.18 (±0.40) | 0.18 (±0.39) | 0.73 (±0.46) | 0.97 | *0.001* | *0.001* |
| GUPI1C | Discomfort in the urethra | 0.18 (±0.40) | 0.22 (±0.43) | 0.73 (±0.46) | 0.80 | *0.001* | *0.001* |
| GUPI1D | Discomfort below the waist | 0.45 (±0.52) | 0.78 (±0.43) | 0.60 (±0.51) | 0.08 | 0.48 | 0.28 |
| GUPI2A | Pain or burning during urination | 0.09 (±0.30) | 0.39 (±0.50) | 0.53 (±0.52) | 0.09 | *0.02* | 0.42 |

TABLE 2-continued

| Question | Symptom feature | NIL (Std Dev) | LI (Std Dev) | EC (Std. Dev) | P (NIL vs. LI) | P (NIL vs. EC) | P (LI vs EC) |
|---|---|---|---|---|---|---|---|
| GUPI2B | Pain or discomfort with sexual intercourse | 0.27 (±0.47) | 0.33 (±0.49) | 0.53 (±0.52) | 0.74 | 0.20 | 0.26 |
| GUPI2C | Pain or discomfort as your bladder fills | 0.27 (±0.47) | 0.67 (±0.49) | 0.27 (±0.46) | *0.04* | 0.97 | *0.02* |
| GUPI2D | Pain or discomfort relieved by voiding | 0.27 (±0.47) | 0.53 (±0.51) | 0.27 (±0.46) | 0.19 | 0.97 | 0.14 |
| GUPI3 | How often was your pain | 1.91 (±2.07) | 2.63 (±1.50) | 2.60 (±1.88) | 0.31 | 0.38 | 0.97 |
| GUPI4 | Average pain or discomfort | 2.91 (±2.91) | 4.83 (±2.07) | 3.80 (±3.05) | *0.05* | 0.46 | 0.26 |
| GUPI Pain | Total GUPI 1-4 | 5.77 (±7.25) | 9.89 (±4.97) | 9.47 (±7.01) | 0.06 | 0.17 | 0.83 |
| GUPI5 | Sensation of not emptying your bladder | 1.18 (±1.60) | 2.50 (±1.86) | 1.60 (±1.55) | 0.06 | 0.51 | 0.15 |
| GUPI6 | Urinate again within two hours | 2.73 (±2.15) | 3.56 (±0.92) | 3.33 (±1.76) | 0.16 | 0.44 | 0.64 |
| GUPI Urinary | Total GUPI 5-6 | 3.31 (±3.52) | 5.74 (±2.70) | 4.35 (±3.22) | *0.04* | 0.40 | 0.17 |
| GUPI7 | Impact on activities | 0.91 (±1.22) | 1.83 (±1.04) | 1.40 (±1.24) | *0.04* | 0.33 | 0.28 |
| GUPI8 | Distraction by symptoms | 1.45 (±1.37) | 2.58 (±0.81) | 2.33 (±0.82) | *0.01* | 0.05 | 0.39 |
| GUPI9 | Satisfaction with current symptoms | 3.27 (±2.53) | 4.50 (±1.15) | 4.40 (±1.18) | 0.08 | 0.14 | 0.81 |
| GUPI Bother | Total GUPI 7-9 | 4.77 (±4.85) | 8.45 (±3.11) | 7.18 (±3.76) | *0.01* | 0.14 | 0.28 |
| GUPI Total | Total GUPI 1-9 | 13.85 (±14.85) | 24.08 (±8.08) | 21.00 (±12.25) | *0.02* | 0.16 | 0.37 |
| PFDI20_1 | Pressure in the lower abdomen | 1.38 (±1.85) | 1.69 (±1.55) | 1.63 (±1.78) | 0.65 | 0.73 | 0.92 |
| PFDI20_2 | Heaviness or dullness in the abdomen | 1.69 (±1.60) | 1.46 (±1.56) | 1.19 (±1.60) | 0.71 | 0.41 | 0.65 |
| PFDI20_3 | Vaginal bulge | 0.15 (±0.38) | 0.31 (±0.85) | 0.69 (±1.40) | 0.25 | 0.12 | 0.40 |
| PFDI20_4 | Splint to defecate | 0.08 (±0.28) | 0.46 (±1.20) | 0.47 (±1.13) | 0.27 | 0.24 | 0.99 |
| PFDI20_5 | Feeling of incomplete emptying | 1.85 (±1.52) | 2.00 (±1.78) | 1.27 (±1.22) | 0.81 | 0.27 | 0.21 |
| PFDI20_6 | Splinting to void | 0.08 (±0.28) | 0.08 (±0.28) | 0.19 (±0.75) | 0.33 | 0.62 | 0.38 |
| POPDI-6 | Total PFDI 1-6 | 5.08 (±4.48) | 4.05 (±4.43) | 5.00 (±4.50) | 0.53 | 0.96 | 0.53 |
| PFDI20_7 | Straining to have a bowel movement | 1.62 (±1.04) | 1.38 (±1.66) | 0.94 (±1.18) | 0.68 | 0.12 | 0.40 |
| PFDI20_8 | Tenesmus | 1.69 (±0.75) | 1.25 (±1.48) | 1.53 (±0.92) | 0.35 | 0.623 | 0.55 |
| PFDI20_9 | Loss of formed stool | 0.15 (±0.55) | 0.33 (±1.15) | 0.13 (±0.50) | 0.62 | 0.88 | 0.52 |
| PFDI20_10 | Loss of liquid stool | 0.38 (±1.12) | 0.46 (±1.20) | 0.31 (±0.87) | 0.87 | 0.85 | 0.70 |
| PFDI20_11 | Flatal incontinence | 0.54 (±1.20) | 0.58 (±1.24) | 0.69 (±0.95) | 0.93 | 0.71 | 0.80 |
| PFDI20_12 | Pain with bowel movements | 1.15 (±1.07) | 0.18 (±0.29) | 0.63 (±1.02) | *0.002* | 0.19 | 0.09 |
| PFDI20_13 | Urgency to have a bowel movement | 1.15 (±1.41) | 0.38 (±0.96) | 0.94 (±1.12) | 0.12 | 0.65 | 0.17 |
| PFDI20_14 | Rectal prolapse | 0.17 (±0.58) | 0.23 (±0.83) | 0.27 (±0.70) | 0.83 | 0.70 | 0.90 |
| CRADI-8 | Total PFDI 7-14 | 6.85 (±4.76) | 3.11 (±5.28) | 5.00 (±4.78) | *0.05* | 0.30 | 0.27 |
| PFDI20_15 | Frequent urination | 2.80 (±1.79) | 2.75 (±1.06) | 2.07 (±1.58) | 0.94 | 0.39 | 0.21 |
| PFDI20_16 | Urine leakage with urgency | 2.40 (±1.67) | 1.50 (±1.93) | 0.93 (±1.28) | 0.38 | 0.05 | 0.37 |
| PFDI20_17 | Urine leakage related to cough, laugh, sneeze | 0.40 (±0.89) | 1.33 (±1.78) | 1.60 (±1.55) | 0.29 | 0.12 | 0.68 |
| PFDI20_18 | Small amounts of urine loss | 1.60 (±1.14) | 1.50 (±1.93) | 0.73 (±1.22) | 0.92 | 0.18 | 0.22 |
| PFDI20_19 | Difficulty emptying your bladder | 0.40 (±0.89) | 0.92 (±1.61) | 0.81 (±1.17) | 0.51 | 0.48 | 0.83 |
| PFDI20_20 | Pain or discomfort in lower abdomen | 1.40 (±1.95) | 1.54 (±1.61) | 1.53 (±1.81) | 0.88 | 0.89 | 0.99 |

TABLE 2-continued

| Question | Symptom feature | NIL (Std Dev) | LI (Std Dev) | EC (Std. Dev) | P (NIL vs. LI) | P (NIL vs. EC) | P (LI vs EC) |
|---|---|---|---|---|---|---|---|
| UDI-6 | Total PFDI 15-20 | 3.46 (±5.77) | 6.16 (±6.48) | 6.82 (±5.87) | 0.24 | 0.13 | 0.75 |
| Age | Years | 41.1 (±15.2) | 37.7 (±15.7) | 37.8 (±6.3) | 0.56 | 0.43 | 0.99 |

Evaluation of Microbial Urotypes as Diagnostic Biomarkers

Figure 5A:
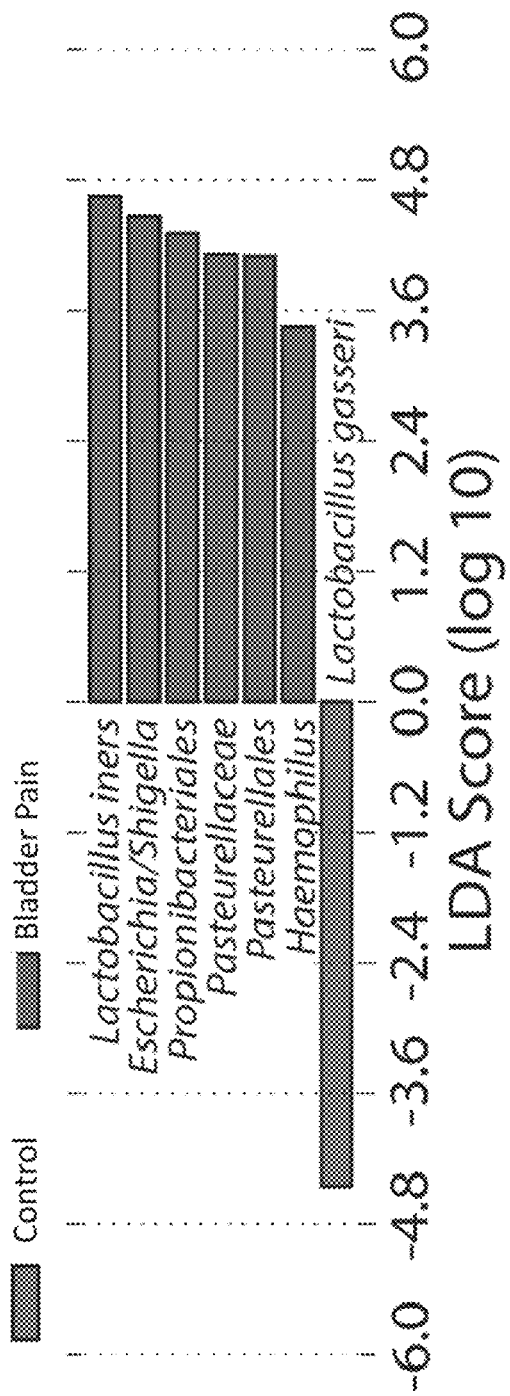
FIG. 5A-5C shows microbial associations persist even after correction for confounders and multiple comparisons. (5A) Linear discriminant analysis (LDA) assesses the statistical and biological relevance of specific taxa as biomarkers for pelvic pain. Differential bacterial features are ranked by linear discriminant analysis effect size (LEfSe), with green and red indicating associations with pain or the asymptomatic state, respectively. A threshold of 4.0 on the logarithmic LDA score was used to identify taxa that significantly differed in abundance between IC/BPS and control subjects. (5B,5C) Box and whisker plots demonstrate the differences in *L. iners* and *E. coli* abundance in the BPS, NUPP, and MFP subgroups after controlling for age, BMI, and hormonal supplementation using Multivariate Association with Linear Models (MaAsLin).
Figure 5C:
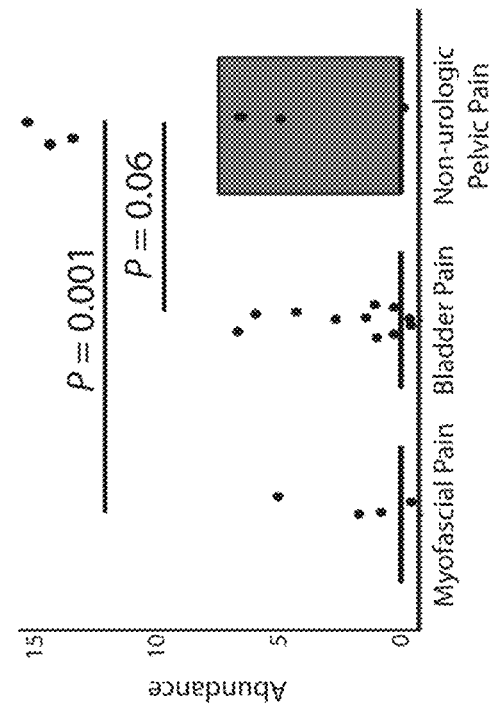
Figure 5B:
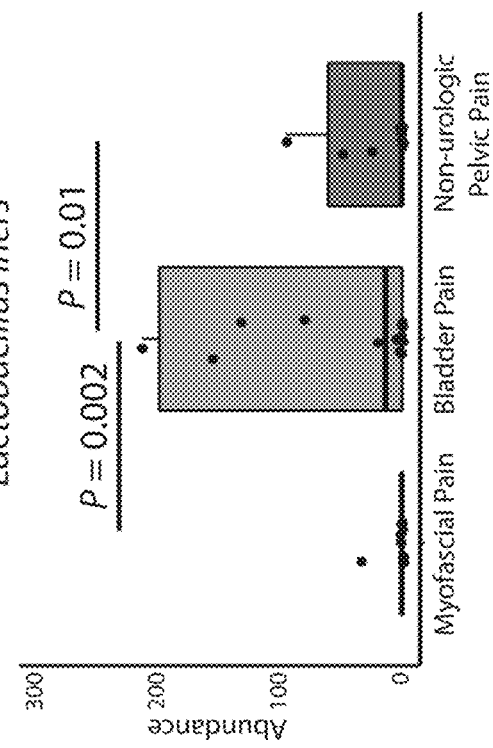

As additional taxa, such as *Vibrio* and *Halomonas*, also segregated with urotype, we used linear discriminant analysis (LDA) to determine the optimal taxa for IC/BPS diagnosis (FIG. 5A). This analysis confirmed *L. iners* and *Escherichia* as the only bacterial taxa exceeding an LDA effect size of 4, confirming their clinical utility in IC/BPS diagnosis. Conversely, L. gasseri, a commensal non-*iners Lactobacillus*, was associated with controls. To assess the utility of these bacteria as markers of individual IC/BPS phenotypes, we utilized Multivariate Association with Linear Models (MaAsLin) to examine associations between symptomatic profiles and microbial abundance. Controlling for confounding variables of age, BMI, and hormonal medications, MaAsLin confirmed the association of LI with BPS and EC with NUPP (FIG. 5). No bacterial taxa were significantly associated with the MFP phenotype when asymptomatic controls were included in the analysis.

Figure 6A:
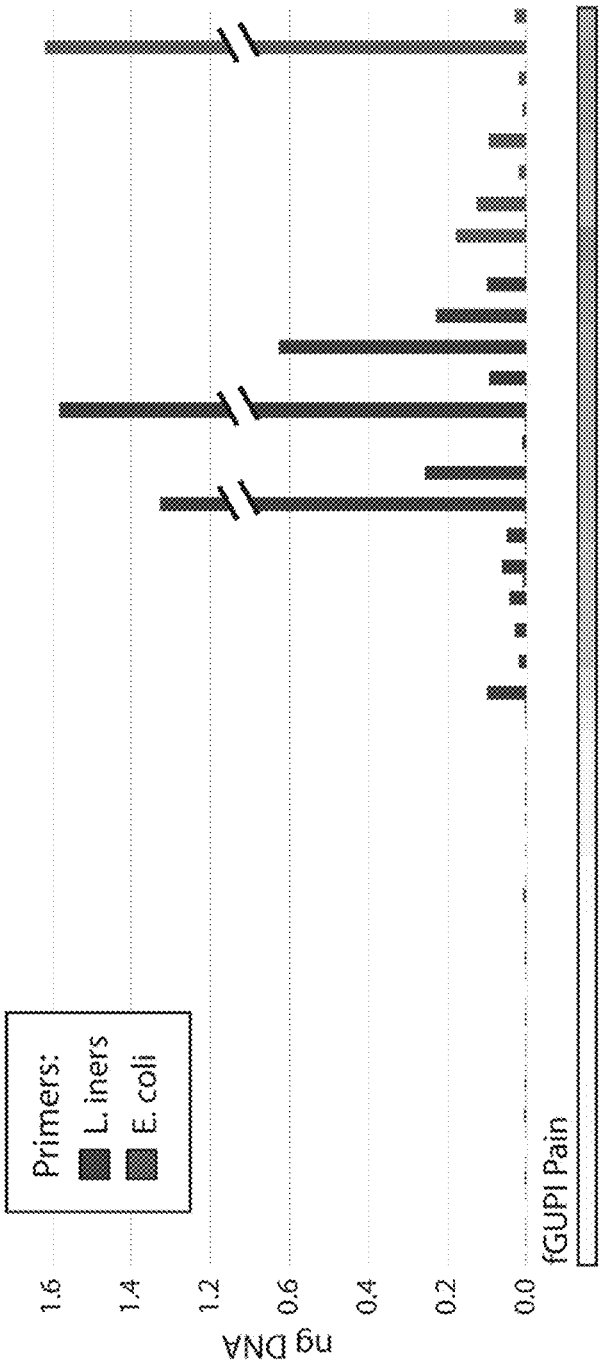
FIG. 6A-6B shows that quantitative PCR provides rapid, scalable testing with objective thresholds to facilitate patient diagnosis and sub-classification. (6A) Using the female Genitourinary Pain Index (fGUPI) as an indicator of patients presenting with and without pain, expressed in the heat bar below the graph, quantitative PCR detecting *Lactobacillus iners* and *Escherichia coli* accurately separated patients with bladder-related pain from asymptomatic controls. (6B) These two microbial markers alone could subclassify unselected patients into distinct groups with diagnostically useful thresholds, as indicated by the dotted lines on each scatter plots of the absolute DNA quantities for each species.
Figure 6B:
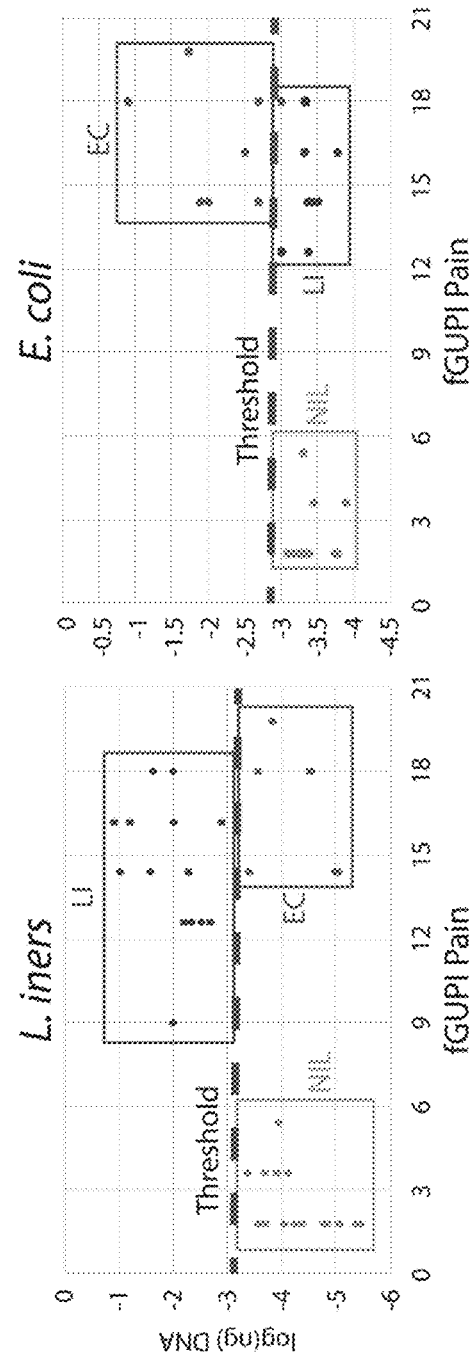

Quantitative Identification of Bacteria in Catheterized Urine from Patients with IC/BPS and Controls While highly sensitive, NGS overestimates microbial diversity, is unreliable for species identification, and provides only relative abundance within a community. To develop a quantitative test for IC/BPS-associated microbial biomarkers, we evaluated species-specific qPCR with validated primers for *L. iners* and *E. coli* (FIG. 6A). Rescreening of our pilot population verified the NGS results, confirming the NIL abundance in controls. Elevated levels of LI in BPS and EC in NUPP demonstrated clear, clinically relevant thresholds (FIG. 6B), suggesting targeted, rapid microbial profiling has clinical potential in IC/BPS phenotyping.

Inflammatory Profiling of the IC/BPS Subgroups Reveals Distinct Inflammatory Associations Alterations in the microbiome often influence human disease through modulation of host inflammatory responses. We therefore examined urinary and serum levels of 40 inflammatory biomarkers in our population of 84 subjects classified by urotype (FIG. 7). The LI urotype exhibited serum elevations in several chemokines, monocyte chemoattractant protein-1 (MCP1/CCL2, p=0.0001), macrophage-derived chemokine (MDC/CCl22, p=0.006) and Eotaxin (CCL11, p=0.02), that distinguished LI from controls and other IC/BPS subjects. The EC urotype exhibited decreased urinary IL-17A (p=0.04) and IL-22 (p=0.04) and increased urinary IL-15 (p=0.01) in comparison to the other groups. In contrast, none of the growth factors or immune mediators examined were significantly different between NIL IC/BPS subjects and both NIL controls and other IC/BPS urotypes. These inflammatory profiles clearly separated the IC/BPS phenotypes defined by urotype, supporting the concept of unique pathophysiologies and lending credibility to the concept that altered inflammation in IC/BPS may be mediated by host-microbe interactions.

Various embodiments of the invention are described above in the Detailed Description. While these descriptions directly describe the above embodiments, it is understood that those skilled in the art may conceive modifications and/or variations to the specific embodiments shown and described herein. Any such modifications or variations that fall within the purview of this description are intended to be included therein as well. Unless specifically noted, it is the intention of the inventors that the words and phrases in the specification and claims be given the ordinary and accustomed meanings to those of ordinary skill in the applicable art(s).

The foregoing description of various embodiments of the invention known to the applicant at this time of filing the application has been presented and is intended for the purposes of illustration and description. The present description is not intended to be exhaustive nor limit the invention to the precise form disclosed and many modifications and variations are possible in the light of the above teachings. The embodiments described serve to explain the principles of the invention and its practical application and to enable others skilled in the art to utilize the invention in various embodiments and with various modifications as are suited to the particular use contemplated. Therefore, it is intended that the invention not be limited to the particular embodiments disclosed for carrying out the invention.

While particular embodiments of the present invention have been shown and described, it will be obvious to those skilled in the art that, based upon the teachings herein, changes and modifications may be made without departing from this invention and its broader aspects and, therefore, the appended claims are to encompass within their scope all such changes and modifications as are within the true spirit and scope of this invention. It will be understood by those within the art that, in general, terms used herein are generally intended as "open" terms (e.g., the term "including" should be interpreted as "including but not limited to," the term "having" should be interpreted as "having at least," the term "includes" should be interpreted as "includes but is not limited to," etc.).

As used herein the term "comprising" or "comprises" is used in reference to compositions, methods, and respective component(s) thereof, that are useful to an embodiment, yet open to the inclusion of unspecified elements, whether useful or not. Although the open-ended term "comprising," as a synonym of terms such as including, containing, or having, is used herein to describe and claim the invention, the present invention, or embodiments thereof, may alternatively be described using alternative terms such as "consisting of" or "consisting essentially of."

What is claimed is:

1. A method of detecting levels of one or more microorganisms in a female subject in need thereof, comprising:
   assaying a biological sample obtained from the female subject, wherein the female subject has one or more symptoms of interstitial cystitis, pelvic pain or bladder pain; and
   detecting the levels of one or more microorganisms in the biological sample,
   wherein the biological sample is urine, and
   wherein the one or more microorganisms comprise *Lactobacillus* species.

2. The method of claim 1, wherein the one or more microorganisms further comprise *Enterobacteriaceae* bacteria.

3. The method of claim 1, wherein the *Lactobacillus* species comprises *Lactobacillus iners* (*L. iners*).

4. The method of claim 1, wherein the female subject also has symptoms of myofascial pain.

5. The method of claim 4, wherein the one or more microorganisms also comprise non-iners *Lactobacilli* (NIL), *Enterobacteriaceae*, or *Shigella*.

6. The method of claim 5, wherein the *Lactobacillus* species comprises *Lactobacillus iners* (*L. iners*).

7. The method of claim 1, wherein the one or more microorganisms also comprise non-*iners Lactobacilli* (NIL), *E. coli*, or *Shigella*.

8. The method of claim 7, wherein the *Lactobacillus* species comprises *Lactobacillus iners* (*L. iners*).

9. The method of claim 1, further comprising comparing each detected level of the one or more microorganisms to each microorganism's reference level.

10. The method of claim 1, wherein the female subject does not have an active urinary tract infection as defined by a negative bacterial culture.

11. The method of claim 1, wherein the assay comprises using a technique selected from the group consisting of qPCR, RT-PCR, and next-generation sequencing.

12. The method of claim 1, wherein the *Lactobacillus* species comprises *Lactobacillus iners* (*L. iners*), and the one or more microorganisms also comprise *E. coli*.

13. The method of claim 1, wherein the one or more microorganisms also comprise *E. coli*.

14. A method for treating a female subject having interstitial cystitis, pelvic pain or bladder pain, comprising:
   administering a bladder instillation to the female subject who has been detected to have a level of *Lactobacillus iners* (*L. iners*) higher than a reference level for *L. iners* in a urine sample.

15. The method of claim 14, further comprising:
   obtaining or requesting the results of an analysis of levels of one or more microorganisms in the urine sample obtained from the female subject before administering the bladder instillation.

16. The method of claim 15, the bladder instillation comprises instilling an agent selected from the group consisting of alkalinized lidocaine and heparin, dimethyl sulfoxide (DMSO), sodium hyaluronate, heparin, a bladder cocktail, PSD597, URG101, sterile sodium chondroitin sulfate solution 2.0%, misoprostol, and combinations thereof.

17. The method of claim 16, the bladder cocktail comprises bupivacaine, heparin, hydrocortisone, lidocaine jelly, triamcinolone, gentamicin, lidocaine, sodium bicarbonate, DMSO, or combinations thereof.

18. The method of claim 14, wherein the female subject does not have an active urinary tract infection as defined by a negative bacterial culture.

19. The method of claim 14, wherein *Lactobacillus iners* (*L. iners*) is detected by using a technique selected from the group consisting of qPCR, RT-PCR, and next-generation sequencing.

20. A method for treating interstitial cystitis, pelvic pain, bladder pain, or myofascial pain, comprising:
   administering a musculoskeletal-directed therapy to a subject who has been detected, in a urine sample obtained from the subject, to have both a level of *Lactobacillus iners* (*L. iners*) lower than a reference level for *L. iners*, and a level of *E. coli* lower than a reference level for *E. coli*.

21. A method of selecting a treatment for a female subject having interstitial cystitis, pelvic pain, bladder pain, or myofascial pain comprising
   detecting levels of one or more microorganisms in a urine sample obtained from the female subject in need thereof; and
   selecting bladder instillation treatment for the female subject having levels of *Lactobacillus iners* (*L. iners*) that are higher than a reference level for *L. iners* in the urine sample, or
   selecting a musculoskeletal-directed therapy for the female subject who has been detected to have both a level of *Lactobacillus iners* (*L. iners*) lower than a reference level for *L. iners* in urine, and a level of *E. coli* lower than a reference level for *E. coli* in urine, and
   administering the selected bladder instillation or the selected musculoskeletal-directed therapy.

* * * * *